(12) United States Patent
Horn et al.

(10) Patent No.: US 9,968,594 B2
(45) Date of Patent: *May 15, 2018

(54) COMPOSITIONS AND METHODS FOR THE TREATMENT OF PRESBYOPIA

(71) Applicant: Presbyopia Therapies, LLC, Coronado, CA (US)

(72) Inventors: Gerald Horn, Deerfield, IL (US); Lee Nordan, Dana Point, CA (US)

(73) Assignee: Presbyopia Therapies LLC, Coronado, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/860,770

(22) Filed: Sep. 22, 2015

(65) Prior Publication Data

US 2016/0008337 A1 Jan. 14, 2016

Related U.S. Application Data

(63) Continuation-in-part of application No. 14/742,903, filed on Jun. 18, 2015, now Pat. No. 9,320,709, which is a continuation-in-part of application No. 14/223,639, filed on Mar. 24, 2014, now Pat. No. 9,089,562.

(60) Provisional application No. 61/938,438, filed on Feb. 11, 2014, provisional application No. 61/917,620, filed on Dec. 18, 2013, provisional application No. 61/904,510, filed on Nov. 15, 2013, provisional application No. 61/882,998, filed on Sep. 26, 2013, provisional application No. 61/871,215, filed on Aug. 28, 2013.

(51) Int. Cl.

| | |
|---|---|
| A61K 31/4409 | (2006.01) |
| A61K 31/4178 | (2006.01) |
| A61K 31/439 | (2006.01) |
| A61K 45/06 | (2006.01) |
| A61K 31/165 | (2006.01) |
| A61K 31/4164 | (2006.01) |
| A61K 31/498 | (2006.01) |
| A61K 9/00 | (2006.01) |

(52) U.S. Cl.
CPC ........ *A61K 31/4409* (2013.01); *A61K 9/0048* (2013.01); *A61K 31/165* (2013.01); *A61K 31/4164* (2013.01); *A61K 31/4178* (2013.01); *A61K 31/439* (2013.01); *A61K 31/498* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,291,466 B1 | 9/2001 | Gwon et al. | |
| 6,410,544 B1 | 6/2002 | Gwon et al. | |
| 8,299,079 B2 | 10/2012 | Kaufman | |
| 8,455,494 B2 | 6/2013 | Kaufman | |
| 8,501,800 B2 | 8/2013 | Bowman et al. | |
| 2006/0177430 A1 | 8/2006 | Bhushan et al. | |
| 2010/0016395 A1 | 1/2010 | Benozzi | |
| 2011/0251285 A1* | 10/2011 | Tien | A01N 47/44 514/635 |
| 2012/0094962 A1 | 4/2012 | Skulachev | |
| 2013/0245030 A1 | 9/2013 | Kaufman | |

FOREIGN PATENT DOCUMENTS

| | | |
|---|---|---|
| WO | 2002/100437 A2 | 12/2002 |
| WO | 2009/077736 A2 | 6/2009 |
| WO | 2010/135731 A1 | 12/2010 |
| WO | 2013/041967 A2 | 3/2013 |

OTHER PUBLICATIONS

Grunberger, J., et al., The pupillary response test as a method to differentiate various types of dementia, Neuropsychiatr, 2009, 23(1), 52-57.
Ward, J.S., et al., 1,2,5-Thiadiazole analogues of aceclidine as potent m1 muscarinic agonists, J Med Chem, Jan. 29, 1988, 41(3), 379-392.
Berge, S. M., et al., "Pharmaceutical Salts", Journal of Pharmaceutical Science, 1977, 66, 1-19.
International Search Report and Written Opinion for corresponding PCT Application No. PCT/US2014/052256 dated Dec. 18, 2014.
AKORN Incorporated MSDS:Tropicacyl (R); Rev. 11-11.
MAYO Clinic: Tropicamide (Opthalmic Route), 2015, http://www.mayoclinic.org/drugs-supplements/tropicamide-ophthalmic-route/description/drg-20066481.
Chung, S.T. et al., The effect of dioptric blur on reading performance, Vision Res, Jun. 2007, 47(12), 1584-94.
Cowan, E.C. et al., Clinical evaluation of a new mydriatic-mydrilate, Br J Ophthalmol, Dec. 1962, 46(12), 730-6.
Davidson, S., General medicine and visual side effects, Br Med J, Mar. 24, 1979, 1(6166), 821.
Drance, S.M., Dose response of human intraocular pressure to aceclidine, Arch Ophthalmol, Oct. 1972, 88(4), 394-6.
Edwards, R.S., Behaviour of the fellow eye in acute angle-closure glaucoma, Br J Ophthalmol, Sep. 1982, 66(9), 576-9.
Gardiner, P.A., ABC of Ophthalmology: Methods of examination, Br Med J, Dec. 9, 1978, 2(6152),1622-6.
Gardiner, P.A., ABC of Ophthalmology: accidents and first aid, Br Med J, Nov. 11, 1978, 2(6148),1347-50.
Hoyng, F.J., The combination of guanethidine 3% and adrenaline 0.5% in 1 eyedrop (GA) in glaucoma treatment, Br J Ophthalmol, Jan. 1979, 63(1), 56-62.

(Continued)

*Primary Examiner* — David J Blanchard
*Assistant Examiner* — Sarah Chickos
(74) *Attorney, Agent, or Firm* — Wood, Phillips, Katz, Clark & Mortimer

(57) ABSTRACT

The invention provides compositions and methods for the treatment of presbyopia. In a preferred embodiment correction of presbyopia occurs without reduction in distance vision acuity. The compositions of the invention preferably contain a muscarinic agonist and a cycloplegic agent.

19 Claims, 2 Drawing Sheets

(56) References Cited

OTHER PUBLICATIONS

Mohan, K., Optimal dosage of cyclopentolate 1% for cycloplegic refraction in hypermetropes with brown irides, Indian J Ophthalmol, Nov.-Dec. 2011, 59(6), 514-6.
Nayak, B.K., A comparison of cycloplegic and manifest refractions on the NR-1000F (an objective Auto Refractometer), Br J Ophthalmol, Jan. 1987, 71(1), 73-5.
Park, J.H., The comparison of mydriatic effect between two drugs of different mechanism, Korean J Ophthalmol Mar. 2009, 23(1), 40-2.
Romano, J.H., Double-blind cross-over comparison of aceclidine and pilocarpine in open-angle glaucoma, Br J Ophthalmol, Aug. 1970, 54(8), 510-21.
Smith, S.A., Subsensitivity to cholinoceptor stimulation of the human iris sphincter in situ following acute and chronic administration of cholinomimetic miotic drugs, Br J Pharmacol, Jul. 1980, 69(3), 513-8.
Tataru, C.P., Antiglaucoma pharmacotherapy, J Med Life, Sep. 15, 2012, 5(3), 247-51.
Trinavarat, A., Effective pupil dilatation with a mixture of 0.75% tropicamide and 2.5% phenylephrine: A randomized controlled trial, Indian J Ophthalmol, Sep.-Oct. 2009, 57(5), 351-4.
Wood, J.M., Pupil dilatation does affect some aspects of daytime driving performance, Br J Ophthalmol, Nov. 2003, 87(11), 1387-90.
Fechner, P.U., et al., Accomodative effects of aceclidine in the treatment of glaucoma, Amer J Ophth. Jan. 1975, 79(1) 104-106.

\* cited by examiner

COMPOSITIONS AND METHODS FOR THE TREATMENT OF PRESBYOPIA

BACKGROUND OF THE INVENTION

As a person ages the minimum distance from the eye at which an object will come into focus, provided distance vision is corrected or is excellent unaided, increases. For example, a 10 year-old can focus on an object or a "focal point" only three inches (0.072 meters) from their eye while still retaining excellent distance vision; a 40 year-old at six inches (0.15 meters); and a 60 year-old at an inconvenient 39 inches (1.0 meter). This condition of increasing minimum focal length in individuals with excellent unaided distance vision is called presbyopia, loosely translated as "old-man eye".

Excellent unaided distance vision is also known as emmetropia. The inability to focus on distant focal points is known as myopia and the inability to focus on near focal points is known as hyperopia. Specifically, "distance" vision is considered any focal point 1 meter or more from the eye and near vision is any focal point less than 1 meter from the eye. The minimum focal length at which an object will come into focus is known as the "near point". The change in focus from distance to the near point and any focal point in between is called accommodation. Accommodation is often measured in diopters. Diopters are calculated by taking the reciprocal of the focal length (in meters). For example, the decrease in accommodation from a 10 year-old eye to a 60 year-old eye is about 13 diopters ($1 \div 0.072$ meters=13.89 diopters; $1 \div 1$ meter=1 diopter).

The highest incidence of first complaint of presbyopia occurs in people ages 42-44. Presbyopia occurs because as a person ages the eye's accommodative ability which uses near reflex-pupil constriction, convergence of the eyes and particularly ciliary muscle contraction decreases. This reduction in accommodation results in an inadequate change in the normal thickening and increased curvature of the anterior surface of the lens that is necessary for the shift in focus from distant objects to near objects. Important near focus tasks affected by presbyopia include viewing computer screens (21 inches) and reading print (16 inches).

Presbyopia is a normal and inevitable effect of ageing and is the first unmistakable sign for many in their forties that they are getting older. One study found that more than 1 billion people worldwide were presbyopic in 2005. This same study predicted that number to almost double by the year 2050. If everyone over the age of 45 is considered to be presbyopic, then an estimated 122 million people in the United States alone had presbyopia in 2010. As baby boomers reach the critical age, this number is only going to increase.

Presbyopia carries with it a stigma resulting from the limitation in ability to quickly function at many tasks requiring focusing at both distant and near points, which once occurred almost immediately. In the presbyopic patient, these tasks can be performed only by the use of eyeglasses, contact lenses or after undergoing invasive surgery. One such optical modification, the monovision procedure, can be executed with the use of glasses, contact lenses or even surgery. The monovision procedure corrects one eye for near focus and the other eye for distance focus. However, monovision correction is normally accompanied by loss of depth perception and distance vision particularly in dim light (e.g. night). Other surgical procedures that have been developed to relieve presbyopia include: (1) the implantation of intraocular lenses (INTRACOR®; registered trademark of Technolas Perfect Vision GMBH); (2) reshaping of the cornea (PresbyLASIK and conductive keratoplasty); (3) scleral band expansion; and (4) implantation of corneal inlays (Flexivue Microlens®; registered trademark of PresbiBio LLC, Kamra®; registered trademark of AcuFocus, Inc. and Vue+). Kamra® corneal inlays manufactured by AcuFocus work by inlaying a pinhole on the cornea to increase the depth of focus. A similar effect can be achieved with general miotic agents, such as pilocarpine (a non-selective muscarinic acetylcholine receptor agonist), carbachol (a non-selective muscarinic acetylcholine receptor agonist), and phospholine iodide (an acetylcholinesterase inhibitor). These general miotic agents trigger increased ciliary muscle contraction and induce accommodation of any remaining reserves, improving near vision at the expense of distance vision in individuals who still retain some accommodative function. While these general miotic agents also create improved depth of focus via a pinhole effect induced by pupillary miosis (i.e. constriction), to the degree accommodation occurs, the pinhole effect only partially offsets the induced accommodative myopia for distance. In some cases, such as with pilocarpine or carbachol, the induced accommodation may create up to 5 diopters or more of induced myopia resulting in induced myopia causing blurred distance vision generally and during shift of the focal point from distance to near. These general miotic agents also cause substantial redness, severe nasal congestion and create ciliary muscle spasms, which commonly induces discomfort that can be severe and long-lasting. In extreme cases, such ciliary muscle spasms can result in retinal detachment.

The holy grail of topical induced presbyopic correction results in no reduction in distance vision. Currently all miotic agents (e.g. muscarinic agonists) cause a reduction in distance vision by converting points of distance focus to a near point. Miotic agents enhance near vision in this manner through contraction of the ciliary muscle, particularly the circumferential radial component, however this same contraction thereby causes reduction in distance vision. Distance vision is reduced by as much as 5 to 11 diopters (e.g. pilocarpine 2%-4%) in some cases, particularly for those with some residual near focus (accommodation). While this can be modulated by reducing the concentration of the miotic agent, the degree of ciliary induced accommodation is thereby also reduced limiting the closeness of the near point of focus. Further, any advantage of increased depth of focus from pinhole optics that might enhance both distance and near vision requires sufficiently great pupil constriction. This pupil constriction requires higher concentrations of muscarinic agonists than the distance blur resulting from even modest concentrations will allow.

Miotic agents have been described in various patent and patent applications for the treatment of presbyopia. U.S. Pat. Nos. 6,291,466 and 6,410,544 describe the use of pilocarpine to regulate the contraction of ciliary muscles to restore the eye to its resting state and potentially restore its accommodative abilities.

US Patent Application Publication No. 2010/0016395 describes the use of pilocarpine with the non-steroidal anti-inflammatory, diclofenac, to reduce brow ache from ciliary spasm, but does not prevent induced miosis and distance blur. International PCT Application Publication WO/2013/041967 describes the use of pilocarpine with oxymetazoline or meloxicam to temporarily overcome ocular conditions such as presbyopia and possibly slightly decreases the degree of ciliary muscle contraction due to reduced pilocarpine levels in the ciliary body due to vasoconstriction of the ciliary vasculature. Specifically, ciliary induced miosis results in about 0.7 lines of distance vision loss, equating to an eye that is reduced to 20.27 distance vision. This reduction is about a 26% drop in distance acuity from the otherwise 20.20 best corrected vision.

U.S. Pat. No. 8,299,079 (HEK Development LLC) describes the use of direct acting general miotic agents such as pilocarpine, carbachol and phospholine iodide with brimonidine at a concentration from 0.05% to 3.0% w/v. However, the use of brimonidine concentrations at or above 0.05% w/v results in increased dryness and with regular use possible rebound hyperemia. For example, rebound redness occurs in 25% of patients using brimonidine 0.20% w/v (Alphagan®, registered trademark of Allergan, Inc.) twice daily. Further brimonidine only slightly reduces dilation of the pupil in scotopic conditions, does not enhance its constriction or affect ciliary induced myopia.

US Patent Application No. 2014/0113946 (Allergan®) discloses means of treating presbyopia using pilocarpine and an alpha agonist, such as oxymetazoline. Examples using pilocarpine 1.0% disclose a loss of 0.7 lines of average distance vision (26% reduction) and demonstrate pupil constriction greater than 2.0 millimeters ("mm") at all time points, ranging from 2.1 to 3.2 over a six hour period. Oxymetazoline concentrations in preferred embodiments of 0.05% and 0.125% are both at or above concentrations known to be associated with rebound hyperemia (0.05%) and labeled for maximum daily use of three days (Visine L.R.®; Visine L.R. is a registered trademark of Johnson & Johnson Corp.).

These attempts at miotic treatment for presbyopia all induce transient myopia of reducing distance vision by 20% or worse for many subjects, caused by ciliary contraction. These attempts also often induce bothersome and not infrequently painful ciliary brow ache analogous to a moderately severe migraine. In some cases, miotic treatments induce improved near vision that begins deteriorating within a few hours (i.e. US 2014/0113946 loss of effect starting at about 4 hours and degrading rapidly).

Current efforts to achieve presbyopic treatment with miotic agents are limited by the accommodative distance blur and ciliary induced brow ache that severely limit usefulness. Specifically, due to the need for lower concentrations that may somewhat reduce but not eliminate these bothersome side effects, only limited pupillary miosis occurs. This limited pupillary miosis limits depth of focus pinhole optic benefit to near vision and distance vision. Both distance and near optimal vision potential is compromised. Additionally, this limited pupillary miosis is sufficient only to partially offset the distance blur resulting from greater near point of focus. Further, only a few hours duration of this limited action can be achieved. Thus, there is a need in the art for a treatment of presbyopia that is non-invasive and convenient with minimal side effects. Specifically, there is a need for an opthalmological composition that will allow a person suffering from presbyopia to focus on near objects without significant side effects such as diminished distance vision, blurred vision, pain, and redness, impaired night driving or incapacitating dim light vision, induced nasal congestion, or risk of retinal detachment.

SUMMARY OF THE INVENTION

In certain embodiments, the present invention is directed to compositions and methods for the treatment of presbyopia.

In certain embodiments, the present invention is directed to compositions and methods for the treatment of presbyopia comprising a muscarinic agonist, wherein the muscarinic agonist preferentially activates M1 and M3 muscarinic acetylcholine receptors. In still more preferred embodiments the muscarinic agonist is more highly selective for M1 than M3.

In certain embodiments, the present invention is directed to compositions and methods for the treatment of presbyopia comprising a muscarinic agonist that preferentially activates M1 and M3 muscarinic acetylcholine receptors.

In certain embodiments, the present invention is directed to compositions and methods for the treatment of presbyopia comprising a muscarinic agonist that activates only M1 muscarinic acetylcholine receptors.

In certain embodiments, the present invention is directed to compositions for the treatment of presbyopia comprising a muscarinic agonist, preferably selected from the group consisting of pilocarpine, aceclidine, talsaclidine, sabcomeline, cevimeline, WAY-132983, AFB267B (NGX267), AC-42, AC-260584, 77-LH-28-1, and LY593039 or any pharmaceutically acceptable salts, esters, analogues, prodrugs or derivatives thereof and a cycloplegic agent, preferably selected from pirenzepine, tropicamide, cyclopentolate hydrochloride, 4-diphenylacetoxy-N-methylpiperidine methiodide (4-DAMP), AF-DX 384, methoctramine, tripitramine, darifenacin, solifenacin, tolterodine, oxybutynin, ipratropium, oxitropium, tiotropium, otenzepad and a combination thereof.

In certain other embodiments, the present invention is directed to an opthalmological composition of the present invention comprising a muscarinic agonist and a cycloplegic agent in a ratio greater than about 25:1, preferably greater than about 40:1.

In certain embodiments, the present invention is directed to opthalmological compositions for the treatment of presbyopia comprising pilocarpine or any pharmaceutically acceptable salts, esters, analogues, prodrugs or derivatives thereof and a cycloplegic agent, preferably selected from pirenzepine, tropicamide, cyclopentolate hydrochloride, 4-diphenylacetoxy-N-methylpiperidine methiodide (4-DAMP), AF-DX 384, methoctramine, tripitramine, darifenacin, solifenacin, tolterodine, oxybutynin, ipratropium, oxitropium, tiotropium, otenzepad and a combination thereof.

In certain embodiments, the present invention is directed to opthalmological compositions for the treatment of presbyopia comprising pilocarpine at a concentration from about 0.5% to about 2.5% w/v, preferably about 1.5% w/v and a cycloplegic agent at a concentration from about 0.010% to about 0.1% w/v.

In certain embodiments, the present invention is directed to opthalmological compositions for the treatment of presbyopia comprising pilocarpine or any pharmaceutically acceptable salts, esters, analogues, prodrugs or derivatives thereof and tropicamide.

In certain embodiments, the present invention is directed to opthalmological compositions for the treatment of presbyopia comprising pilocarpine at a concentration from about 0.5% to about 2.5% w/v, preferably about 1.5% w/v and 0.95% w/v and tropicamide at a concentration from about 0.010% to about 0.1% w/v, preferably about 0.035% w/v and about 0.015% w/v.

The present invention is further directed to a method for treating presbyopia comprising administering to a patient in need thereof a pharmaceutically effective amount of a composition of the present invention.

The present invention is further directed to a method for treating presbyopia without reducing distance vision acuity comprising administering to a patient in need thereof a pharmaceutically effective amount of a composition of the present invention.

DETAILED DESCRIPTION OF THE INVENTION

Figure 1:
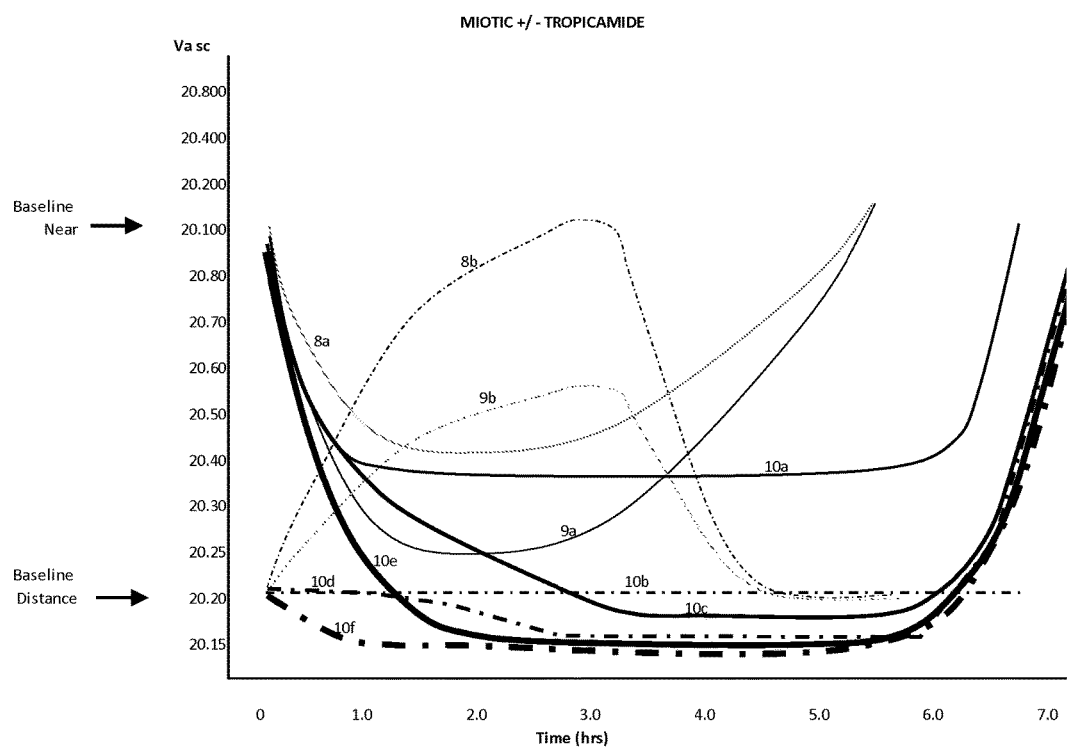
FIG. 1 is a graphical representation of the effects of pilocarpine and aceclidine with or without tropicamide and with or without a carrier on near and distance vision in a patient over the age of 45.

The present invention is directed to compositions and methods of treating presbyopia, irregular astigmatism, and/or refractive error, comprising administering to a patient in need thereof a pharmaceutical composition comprising a muscarinic agonist that preferentially activates M1 and M3 muscarinic acetylcholine receptors, preferably activate M1 more than M3 and most preferably aceclidine or its derivatives. Pilocarpine and aceclidine have been surprisingly and unexpectedly discovered to provide enhanced presbyopic reversal with negligible side effects day or night (when viewing includes one or more direct or reflected light sources) using compositions of the present invention.

Aceclidine is traditionally used as a treatment for glaucoma. When aceclidine is used to treat glaucoma it is normally stored in a two-bottle system; one bottle containing the lyophilized aceclidine and the second bottle containing the diluent necessary to reconstitute the lyophilized aceclidine before topical instillation. Romano J. H., Double-blind cross-over comparison of aceclidine and pilocarpine in open-angle glaucoma, *Brit J Ophthal*, August 1970, 54(8), 510-521. It is a further aspect of the present invention to provide an aqueous aceclidine composition that is stable in combination with cold chain storage. It is yet a further aspect of the present invention to provide a method of stabilizing aqueous aceclidine by combining effective excipients, pH ranges and temperature ranges.

The compositions and methods of the present invention treat presbyopia by improving depth of focus in patients with presbyopia by administering an opthalmological composition to the eye that:
1) reduces pupil dilation in the dark or in dim light;
2) produces a particular degree and duration of miosis without sufficient accommodation to overcome pinhole optic distance vision enhancement;
3) enhances near vision with depth of focus near enhancement further improved by residual sub distance threshold pinhole optic degradation still sufficient to provide additive near benefit; and
4) provides cosmetic whitening and/or induce redness prophylaxis. The compositions and methods of the present invention also do not cause significant pupil rebound, tachyphylaxis, ciliary spasms, induction of myopia or reduction in distance vision. Additionally, the compositions and methods of the present invention allow for the further improvement in visual acuity and depth perception of binocular (both eyes) treatment.

The opthalmological composition of the present invention surprisingly creates a pupil of from about 1.5 to about 2.4 mm at the anterior iris plane and about 2.0 mm at the corneal surface with negligible increase in accommodative tone and with a reduction or ablation of the redness that is otherwise a hallmark of the use of miotic agents. This pupil miosis with greatly diminished or absent accommodative tone is superior to the pinhole effect of the Kamra® and Flexivue Microlens® corneal inlays. Pupil miosis is superior because the constriction of the actual pupil does not result in the attendant severe night vision disturbance caused by the light scattering borders of the pre-corneal pinholes created by the inlays. Further pupil miosis provides a greater field of vision and transmission of more focused light. The use of aceclidine has a minimal effect on the longitudinal ciliary muscle, thus reducing risk of retinal detachment when compared to the use of general muscarinic agonists such as carbachol. The further inclusion of a cycloplegic agent resulted in only 0.04 mm of anterior chamber shallowing. Aceclidine particularly as enhanced for the present invention also has greater magnitude, duration, and control of minimum pupil diameter. Compositions of the present invention achieve these advantages while having negligible effects on accommodation, thus avoiding the distance blur typically seen in patients as a response to pilocarpine and/or carbachol induced miosis. Any effects on accommodation may be further reduced or totally eliminated in preferred embodiments with a cycloplegic agent. Aceclidine is capable of producing the increased depth of focus by pupil miosis described in the present invention without the need of a selective α-2 adrenergic receptor agonist ("α-2 agonist"). Particularly enhanced miosis occurs with use of compositions of the present invention, thus making it possible to use an α-2 agonist at low concentrations to reduce eye redness. Further, due to the apparent and surprisingly selective nature of aceclidine, administration to the eye almost exclusively affects pupil miosis rather than ciliary muscle contraction. Thus, the administration of aceclidine results in pupil miosis without accommodation and attendant distance blur. However, aceclidine may cause some redness and brow ache, and without formulation enhancement of the present invention may produce less than optimal pupil miosis or at extremely high concentration more than desired peak miosis with added dimming of vision in dim or absent lighting.

Certain embodiments of the present invention enhance the discovered preferred degree of pupillary miosis by providing a consistent range of effect of about 1.50-2.20 mm for most patients using a preferred embodiment of a nonionic surfactant and viscosity enhancer. Similar benefit may be achieved using other permeation enhancers, particularly Carbopol® (polyacrylic acid or carbomer), and various viscosity additives that increase drug residence time, such as xanthan gums, guar gum, alginate, and other in situ gels well known to experts in the art. The present invention further prevents nasal congestion otherwise occurring when substantial aceclidine levels reach the nasal mucosa, due to the rheologic properties of the preferred embodiment.

In certain other embodiments, the present invention is directed to an opthalmological composition for the treatment of presbyopia comprising aceclidine.

In certain other embodiments the present invention is directed to an opthalmological composition for the treatment of presbyopia comprising aceclidine and a cycloplegic agent.

In certain other embodiments, the present invention is directed to an opthalmological composition for the treatment of presbyopia comprising aceclidine and a selective α-2 adrenergic receptor agonist.

In certain other embodiments, the present invention is directed to an opthalmological composition for the treatment of presbyopia comprising aceclidine, a cycloplegic agent and a selective α-2 adrenergic receptor agonist.

In certain other embodiments, the present invention is directed to an opthalmological composition for the treatment of presbyopia comprising a general miotic agent and a cycloplegic agent.

In certain other embodiments, the present invention is directed to an opthalmological composition of the present invention comprising:
a general miotic agent, a muscarinic agonist or aceclidine;
  optionally a cycloplegic agent;
  optionally a selective α-2 adrenergic receptor agonist;
  a viscosity enhancer; and
  a surfactant selected from the group consisting of an anionic surfactant, a nonionic surfactant, and a combination thereof.

In one embodiment, the present invention is directed to an opthalmological composition for the treatment of presbyopia comprising:
aceclidine at a concentration from about 0.25% to about 2.0% w/v;
a cycloplegic agent at a concentration from about 0.010% to about 0.1% w/v, preferably selected from pirenzepine, tropicamide, cyclopentolate hydrochloride, 4-diphenylacetoxy-N-methylpiperidine methiodide (4-DAMP), AF-DX 384, methoctramine, tripitramine, darifenacin, solifenacin, tolterodine, oxybutynin, ipratropium, oxitropium, tiotropium, otenzepad and a combination thereof and more preferably tropicamide;
a surfactant, preferably selected from polyoxyl 40 stearate, a gamma cyclodextrin, sulfobutylether β-cyclodextrin, 2-hydroxypropyl cyclodextrin, sodium lauryl sulfate, sodium ester lauryl sulfate, a poloxamer, a polysorbate, sorbitan monolaurate, sorbitan monopalmitate, sorbitan monostearate, sorbitan monooleate, a polyoxyl alkyl, a cyclodextrin and combinations thereof and more preferably polyoxyl 40 stearate;
a tonicity adjustor, preferably selected from mannitol, sodium chloride, potassium chloride, glycerin and combinations thereof and more preferably mannitol; and
optionally a viscosity enhancer, preferably the viscosity enhancer is not a polysaccharide.

In another embodiment, the present invention is directed to an opthalmological composition for the treatment of presbyopia comprising:
aceclidine at a concentration from about 0.25% to about 2.0% w/v;
a cycloplegic agent at a concentration from about 0.010% to about 0.1% w/v;
a surfactant;
a tonicity adjustor; and
one or more excipients selected from a viscosity enhancer selected from the group consisting of guar gum, hydroxypropyl-guar, xanthan gum, alginate, chitosan, Gelrite®, hyauluronic acid, dextran, and a carbomer, preferably carbomer 934 or carbomer 940 wherein the viscosity is from about 1 to about 5,000 centipoise ("cps") prior to topical installation and from about 1 to about 50 cps upon topical installation, preferably from about 1 to about 5,000 cps at from about 2 to about 8° C. and an antioxidant selected from citrate, citric acid monohydrate ethylenediaminetetraacetic acid, disodium ethylenediaminetetraacetic acid, dicalcium diethylenetriamine pentaacetic acid and combinations thereof, preferably citric acid monohydrate.

In a preferred embodiment, the present invention is directed to an opthalmological composition for the treatment of presbyopia comprising:
aceclidine at a concentration from about 0.25% to about 2.0% w/v;
tropicamide at a concentration from about 0.010% to about 0.1% w/v;
polyoxyl 40 stearate at a concentration from about 2.0% to about 10.0% w/v;
mannitol at a concentration from about 0.5% to about 6.0% w/v;
a buffer selected from acetate buffer, citrate buffer, phosphate buffer and citrophosphate buffer at a concentration of about 3 millimolar;
optionally citric acid monohydrate at a concentration from about 0.1% to about 0.2% w/v;
optionally a viscosity enhancer selected from carbomer 934 and carbomer 940 at a concentration from about 0.01% to about 1.0% w/v; and
optionally benzalkonium chloride ("BAK") at a concentration of about 0.02% w/v or a combination of BAK, sorbate and borate,
wherein the pH of the composition is from about 4.75 to about 5.0 and wherein the viscosity of the composition is from about 1 to about 50 cps upon topical installation.

In another preferred embodiment, the present invention is directed to an opthalmological composition for the treatment of presbyopia comprising:
aceclidine at a concentration from about 0.25% to about 2.0% w/v;
tropicamide at a concentration from about 0.010% to about 0.1% w/v;
polyoxyl 40 stearate at a concentration of about 4.0% w/v;
mannitol at a concentration from about 0.5% to about 6.0% w/v;
citric acid monohydrate at a concentration from about 0.1% to about 0.2% w/v;
carbomer 934 at a concentration from about 0.01% to about 1.0% w/v, and
a buffer selected from acetate buffer, citrate buffer, phosphate buffer and citrophosphate buffer at a concentration of about 3 millimolar,
wherein the pH of the composition is about 4.75 and wherein the viscosity of the composition is from about 1 to about 5,000 cps at from about 2 to about 8° C.

In another preferred embodiment, the present invention is directed to an opthalmological composition for the treatment of presbyopia comprising:
aceclidine at a concentration from about 0.25% to about 2.0% w/v;
tropicamide at a concentration from about 0.010% to about 0.1% w/v;
polyoxyl 40 stearate at a concentration of about 5.5% w/v;
mannitol at a concentration of about 4.0% w/v; and
a buffer selected from acetate buffer, citrate buffer, phosphate buffer and citrophosphate buffer at a concentration of about 3 millimolar,
wherein the pH of the composition is about 5.0.

In another preferred embodiment, the present invention is directed to an opthalmological composition for the treatment of presbyopia comprising:
aceclidine at a concentration from about 0.25% to about 2.0% w/v;
tropicamide at a concentration from about 0.010% to about 0.1% w/v;
polyoxyl 40 stearate at a concentration of about 5.5% w/v;
mannitol at a concentration of about 0.5% to about 6% w/v;

citric acid monohydrate at a concentration from about 0.1% to about 0.2% w/v;
carbomer 940 at a concentration from about 0.01% to about 1.0% w/v, and
a buffer selected from acetate buffer, citrate buffer, phosphate buffer and citrophosphate buffer at a concentration of about 3 millimolar,
wherein the pH of the composition is from about 4.75 to about 5.0 and the viscosity of the composition is from about 1 to about 5,000 cps at from about 2 to about 8° C. In some preferred embodiments of the above formulations the aceclidine concentration is about 1.35% to about 1.75% w/v, the mannitol concentration is about 1.0% to 2.5% w/v, and the carbomer 940 concentration is about 0.09% to 1.0% w/v (or equivalent viscosity using any other nonpolysaccharide viscosity agent such as carbomer 934).

The present invention is further directed to a method of treating a refractive error of the eye in a subject in need thereof comprising administering to a subject in need thereof a pharmaceutically acceptable amount of a composition of the present invention wherein the refractive error of the eye is selected from presbyopia, myopia, hyperopia, astigmatism or a combination thereof.

The present invention is further directed to a method for treating presbyopia comprising administering to a patient in need thereof a composition of the present invention.

The present invention is further directed to a method for treating presbyopia without inducing ciliary brow ache comprising administering to a patient in need thereof a pharmaceutically effective amount of a composition of the present invention.

The present invention is further directed to a method for enhancing near vision and distance vision without inducing ciliary brow ache comprising administering to a patient in need thereof a pharmaceutically effective amount of a composition of the present invention.

The present invention is further directed to a method for treating presbyopia via enhancing pinhole optics depth of focus comprising administering to a patient in need thereof a pharmaceutically effective amount of a composition of the present invention.

The present invention is further directed to a method for treating of treating presbyopia via enhancing pinhole optics distance depth of focus and pinhole optics near depth of focus comprising administering to a patient in need thereof a pharmaceutically effective amount of a composition of the present invention, wherein slight ciliary induced myopia occurs without reduction in distance vision.

The present invention is further directed to a method for inducing pupillary miosis focus comprising administering to a patient in need thereof a pharmaceutically effective amount of a composition of the present invention, wherein a substantial reduction in ciliary contraction occurs, an improvement in pinhole optics near depth of focus occurs, near vision and distance vision is improved and ciliary induced brow ache does not occur.

The present invention is further directed to a method for enhancing pinhole optics depth of focus and near vision depth of focus comprising administering to a patient in need thereof a pharmaceutically effective amount of a composition of the present invention, wherein ciliary muscle contraction induced miosis is reduced to a degree that does not reduce distance pinhole optics and wherein, optionally, slight additive accommodation occurs.

The present invention is further directed to a method for treating a refractive error of the eye comprising administering to a patient in need thereof a pharmaceutically acceptable amount of a composition of the present invention, wherein the size of the pupil is reduced to from about 1.5 to about 2.5 millimeters, preferably from about 1.7 to about 2.0 millimeters and wherein the refractive error is selected from the group consisting of corneal irregular astigmatism, an ectasia induced corneal irregularity, a pellucid induced corneal irregularity, a higher order aberration and a refractive surgery induced higher order aberration.

The present invention is further directed to a method of increasing the visual depth of field (i.e. depth of focus) comprising administering to a subject in need thereof a pharmaceutically effective amount of an opthalmological composition of the present invention.

The present invention is further directed to a method of increasing the visual depth perception upon improving near vision unaided comprising administering to a subject in need thereof a pharmaceutically effective amount of an opthalmological composition of the present invention in both eyes (binocular vision), wherein such binocularity further enhances near vision beyond that of either eye separately.

The present invention is further directed to a method of improving vision in a subject with ammetropia (vision abnormality), comprising administering to a subject in need thereof a pharmaceutically effective amount of a composition of the present invention.

The present invention is further directed to a method of improving vision in a subject with ammetropia, comprising administering to a subject in need thereof a pharmaceutically effective amount of a composition of the present invention, wherein ammetropia is selected from the group consisting of nearsightedness, farsightedness, regular astigmatism, irregular astigmatism and high degrees of regular astigmatism.

The present invention is further directed at eliminating optical aberrations induced by corneal irregularity, opacities, or very high degrees of regular astigmatism that include regions adjacent or peripheral to the central 1.5 mm optical zone, and thereby inducing improved visual acuity and quality of vision by filtering out these aberrant optics in those suffering from irregular astigmatism or high degrees of more regular astigmatism, such as occurs in conditions such as keratoconus, photorefractive keratectomy induced corneal haze, diffuse lamellar keratitis ("DLK") (post-lasik DLK), other iatrogenic corneal induced irregularity such as cataract incision, glaucoma filtering blebs, implanted glaucoma valves, corneal inlays with or without removal, ectasia post corneal surgery (lasik), and secondary to infection.

The present invention is further directed at improving acuity relative to existing uncorrected refractive error. Upon this improved acuity, patients now requiring toric contact lenses for astigmatism with reduced comfort and optics that may shift during each blink may in many cases require only non-toric soft contact lenses or no contact lenses. Further, those requiring gas permeable contact lenses may no longer require contact lenses or only require much more comfortable soft contact lenses. Patients with high degrees of astigmatism may now require no correction or reduced astigmatic correction. Patients with small to moderate degrees of nearsightedness may require less correction or no longer require correction. Patients with small to moderate degrees of hyperopia (farsightedness) may require no correction or reduced correction.

The present invention is directed to methods and opthalmological compositions for improving eye sight. In a preferred embodiment the present invention is directed to methods and opthalmological compositions for the treatment of presbyopia. In a more preferred embodiment the present invention is directed to opthalmological compositions comprising aceclidine. In a yet more preferred embodiment present invention is directed to opthalmological compositions comprising aceclidine and a low-dose cycloplegic agent. In a most preferred embodiment the present invention is directed to opthalmological compositions comprising aceclidine, a low-dose cycloplegic agent and a combination of inactive ingredients that make effective and/or enhance aceclidine.

The present invention is further directed to a method for stabilizing the composition of claim 1 comprising maintaining the composition at a temperature from about 2 to about 8° C.

The present invention is further directed to a method for stabilizing an aqueous aceclidine composition comprising the steps of:
  adding a surfactant selected from polyoxyl 40 stearate, a gamma cyclodextrin, sulfobutylether β-cyclodextrin, 2-hydroxypropyl cyclodextrin, sodium lauryl sulfate, sodium ester lauryl sulfate, a poloxamer, a polysorbate, sorbitan monolaurate, sorbitan monopalmitate, sorbitan monostearate, sorbitan monooleate, a polyoxyl alkyl, a cyclodextrin and combinations thereof to the composition, preferably polyoxyl 40 stearate;
  adding a tonicity adjustor selected from mannitol, sodium chloride, potassium chloride, glycerin and combinations thereof, preferably mannitol;
  optionally adding a viscosity enhancer selected from the group consisting of guar gum, hydroxypropyl-guar, xanthan gum, alginate, chitosan, Gelrite®, hyaluronic acid, dextran, a carbomer and combinations thereof to the composition, preferably carbomer 940,
  buffering the pH of the composition to from about 4.0 to about 6.0, preferably 4.75; and
  maintaining the composition at a temperature from about 2 to about 8° C.

The present invention is further directed to a method for stabilizing an aqueous aceclidine composition comprising the steps of:
  adding polyoxyl 40 stearate,
  adding mannitol;
  adding carbomer 940,
  buffering the pH of the composition to 4.75; and
  maintaining the composition at a temperature from about 2 to about 8° C.

The combination of aceclidine and a low concentration of a selective α-2 adrenergic receptor agonist (α-2 agonist or α-2 adrenergic agonist), such as fadolmidine, brimonidine or guanfacine, allows for the desired miotic effect with diminished or no redness. The use of low concentrations of a selective α-2 agonist results in substantial reduction of hyperemia with greatly reduced risk of rebound hyperemia that is found in concentrations of about 0.06% w/v or more. Furthermore, the use of low concentrations of selective α-2 agonist does not adversely modify the pupil constriction caused by aceclidine. In contrast, the use of brimonidine 0.20% w/v, when topically applied for pupil modulation for night vision, result in tachyphylaxis of pupil modulation due to α-2 receptor upregulation in almost 100% of treated subjects within four weeks of use.

Unexpectedly, the addition of a cycloplegic agent results in reduction of any brow ache or associated discomfort by further reducing the degree of ciliary spasms on topical instillation without impairing the miotic response. This lack of impairment of the miotic response is an unexpected surprising discovery, as particular cycloplegic agents, such as tropicamide, have known pupil dilating effects at concentrations as low as 0.01% w/v (Grünberger J. et al., The pupillary response test as a method to differentiate various types of dementia, Neuropsychiatr, 2009, 23(1), pg 57). More specifically cycloplegic agents cause pupil mydriasis (i.e. dilation of the radial muscle of the iris). Further, the addition of a cycloplegic agent to the miotic agent unexpectedly increases the time at which the pupil maintains the desired size range without becoming too restricted. Peak miotic effect at 30-60 minutes can be titrated in inverse relation to the cycloplegic concentration. The concentrations of tropicamide discovered in the present invention apparently cause more relaxation of the ciliary muscle than the iris radial musculature. In fact, iris mydriasis is discovered to be suppressed by the addition of tropicamide to compositions containing concentrations of aceclidine used in the present invention, with instead a more consistent level of miosis for the duration of the miotic effect. Additionally and quite surprisingly, unexpectedly, and beneficially the addition of tropicamide can reduce the degree of peak pupil miosis without inducing mydriasis thereby creating a more constant and ideal pupil size throughout the drug induced miosis. This more consistent pupil size allows for beneficial near and distance vision without the adverse dimming or loss of resolution due to diffraction limits at the very reduced pupil sizes seen at peak pupil miosis (e.g. 1.25 mm).

General miotic agents, such as pilocarpine, carbachol and phospholine diesterase, are capable of causing pupil miosis resulting in improved near vision of presbyopic patients. However, there is an inverse reduction in distance vision associated with these general miotic agents from miosis at peak effect and accommodation that is to a lesser extent also seen with aceclidine. The co-administration of a cycloplegic agent with aceclidine surprisingly results in a complete attenuation of this reduction in distance vision. Additionally, adding a cycloplegic agent to pilocarpine has surprisingly been found to even reduce the greater distance blur normally associated with pilocarpine.

Comfort, safety, and efficacy of a preferred embodiment of an opthalmological composition of the present invention results from the presence of a nonionic surfactant, such as cyclodextrin alpha, beta, or gamma chains, preferably 2-hydroxypropyl beta-cyclodextrin ("HPβCD"), and or sulfobutyl ether derivative of β-cyclodextrin (Captisol®), polyoxyl 40 stearate or poloxamer 407; a viscosity enhancing agent, such as carboxymethyl cellulose ("CMC"); a tonicity adjustor, such as sodium chloride; a preservative, such as benzalkonium chloride and a pH from about 5.0 to about 8.0. Further, an increase in the concentration of the viscosity agent and the electrolyte may result in reduced redness. Specifically, increasing CMC from 0.50% to 0.75% w/v (preferably 0.80% w/v) and sodium chloride from 0.25% to 0.50% w/v results in reduced redness.

The viscosity of compositions of the present invention comprising a viscosity enhancer may be from about 1 to about 5,000 cps prior to topical instillation in the eye. As a result of the shear force applied to the composition as it exits the device used for administration the viscosity is lowered to a range from about 1 to about 50 cps upon topical instillation, preferably from about 15 to about 35 cps.

Definitions

As used herein, the term "composition" is intended to encompass a product comprising the specified ingredients in the specified amounts, as well as any product which results, directly or indirectly, from a combination of the specified ingredients in the specified amounts.

The term "stabilizing", as used herein, refers to any process which facilitates and/or enables an active agent to remain in solution. The term "stabilizing", as used herein, also refers to any means or process which inhibits and/or reduces the tendency of a muscarinic agonist, including aceclidine or pilocarpine, to degrade.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

The term muscarinic receptor agonist ("muscarinic agonist") encompasses agonists that activate muscarinic acetylcholine receptors ("muscarinic receptors"). Muscarinic receptors are divided into five subtypes named M1-M5. Muscarinic agonists of the present invention include those muscarinic agonists that preferentially activate M1 and M3 receptors over M2, M4 and M5 receptors ("M1/M3 agonists"). M1/M3 agonists include but are not limited to pilocarpine, aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrocholoride), N-arylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quiniclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof. A preferred M1/M3 agonist is aceclidine. In a preferred embodiment, muscarinic agonist of the present invention include those muscarinic agonist that preferentially activate M1 and M3 over M2, M4, and M5; and even more preferably activate M1 over M3. In a more preferred embodiment muscarinic agonist of the present invention include those muscarinic agonist that only activate M1.

The term "aceclidine" encompasses its salts, esters, analogues, prodrugs and derivatives including, but not limited to, aceclidine as a racemic mixture, aceclidine (+) enantiomer, aceclidine (−) enantiomer, aceclidine analogues, including, but not limited to, highly M1 selective 1,2,5 thiadiazole substituted analogues like those disclosed in Ward. J. S. et al., 1,2,5-Thiadiazole analogues of aceclidine as potent ml muscarinic agonists, *J Med Chem,* 1998 Jan. 29, 41(3), 379-392 and aceclidine prodrugs including but not limited to carbamate esters.

The term "pilocarpine" encompasses its salts, esters, analogues, prodrugs, derivatives and pilocarpine analogues.

The term "selective α-2 adrenergic receptor agonists" or "α-2 agonist" encompasses all α-2 adrenergic receptor agonists which have a binding affinity of 900 fold or greater for α-2 over α-1 adrenergic receptors, or 300 fold or greater for α-2a or α-2b over α-1 adrenergic receptors. The term also encompasses pharmaceutically acceptable salts, esters, prodrugs, and other derivatives of selective α-2 adrenergic receptor agonists.

The term "low concentrations" or "low-dose" refers to concentrations from between about 0.0001% to about 0.065% w/v; more preferably, from about 0.001% to about 0.035% w/v; even more preferably, from about 0.01% to about 0.035% w/v; and even more preferably, from about 0.03% to about 0.035% w/v.

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, and Alphagan®.

The terms "treating" and "treatment" refer to reversing, alleviating, inhibiting, or slowing the progress of the disease, disorder, or condition to which such terms apply, or one or more symptoms of such disease, disorder, or condition.

The term "pharmaceutically acceptable" describes a material that is not biologically or otherwise undesirable (i.e. without causing an unacceptable level of undesirable biological effects or interacting in a deleterious manner).

As used herein, the term "pharmaceutically effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, a "pharmaceutically effective amount" will depend upon the context in which it is being administered. A pharmaceutically effective amount may be administered in one or more prophylactic or therapeutic administrations.

The term "prodrugs" refers to compounds, including, but not limited to, monomers and dimers of the compounds of the invention, which have cleavable groups and become, under physiological conditions, compounds which are pharmaceutically active in vivo.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

The term "higher order aberrations" refers to aberrations in the visual field selected from starbursts, halos (spherical aberration), double vision, multiple images, smeared vision, coma and trefoil.

The term "cold chain" refers to storage at temperatures from about 2 to about 8° C. from manufacture to immediately prior to administration.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, hyaluronic acid, malic acid, sulphuric acid and phosphoric acid and such organic acids as oxalic acid, malic acid, maleic acid, methanosulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, a heteroaryl group or other suitable substituent.

Compositions of the Invention

In one embodiment, the present invention is directed to an opthalmological composition comprising aceclidine. In a preferred embodiment, aceclidine is at a concentration from about 0.25% to about 2.0% w/v, more preferably from about 0.50% to about 1.90% w/v, still more preferably from about 1.25% to about 1.85% w/v, and most preferably from about 1.35% to about 1.65% w/v. As aceclidine is a tertiary amine with asymmetry, both a + and − optical isomer exist (where in some studies (+) is more potent and in others it is felt (−) may be more potent). For the above concentrations polarimetry demonstrated an exactly equal ratio of (+) and (−) isomer for these concentrations. Altering this ratio could therefore alter this concentration range proportional to a change in ratio.

The present invention is further directed to an opthalmological composition comprising a muscarinic agonist, preferably a nonionic surfactant above its critical micellar concentration for the composition, and a viscosity enhancing agent; or alternatively an in situ gelling agent. In preferred embodiments the initial viscosity of the composition on topical application is above 20 cps, preferably 50 cps, and more preferably above 70 cps at low shear (1/s).

Nonionic surfactants suitable for the present invention include cyclodextrins, polyoxyl alkyls, poloxamers or combinations thereof, and may include in addition combinations with other nonionic surfactants such as polysorbates. Preferred embodiments include polyoxyl 40 stearate and optionally Poloxamer 188, Poloxamer 407, Polysorbate 20, Polysorbate 80, ionically charged (e.g. anionic) beta-cyclodextrins with or without a butyrated salt (Captisol®) 2-hydroxypropyl beta cyclodextrin ("HPβCD"), alpha cyclodextrins, gamma cyclodextrins, Polyoxyl 35 castor oil, and Polyoxyl 40 hydrogenated castor oil or combinations thereof. Further, substitution of other nonionic surfactants compatible with opthalmological use allows for similar formulation advantages, which may included but is not limited to one or more of a nonionizing surfactant such as poloxamer, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxyl, polyoxyl stearate, nonoxynol, octyphenol ethoxylates, nonyl phenol ethoxylates, capryols, lauroglycol, PEG, Brij® 35 (polyoxyethyleneglycol dodecyl ether; Brij is a registered trademark of Uniqema Americas LLC), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl)methyl-2-aminoethane sulfonic acid (TES), 2-Amino-2-hydroxymethyl-propane-1,3-diol (Tris), tyloxapol, and Span® 20-80 (sorbitan monolaurate, sorbitan monopalmitate, sorbitan monostearate, and sorbitan monooleate). In certain embodiments the addition of an anionic surfactant such as sodium lauryl sulfate and or sodium ester lauryl sulfate may be preferred.

Ophthalmological in situ gels which may be substituted for or added in addition to one or more nonionic surfactants include but are not limited to gelatin, carbomers of various molecular weights including carbomer 934 P and 974 P, xanthan gums, alginic acid (alginate), guar gums, locust bean gum, chitosan, pectins and other gelling agents well known to experts in the art.

In preferred embodiments the nonionic surfactant is polyoxyl 40 stearate at a concentration from about 1 to about 15% w/v, more preferably at about 5.5% w/v.

In such preferred embodiment, polyoxyl 40 stearate is found to enhance the redness reduction effect preferentially over aqueous solutions and other nonionic surfactants such as poloxamer 407, particularly in the presence of an α-2 agonist.

Viscosity enhancers suitable for the present invention include, but are not limited to, guar gum, hydroxypropylguar ("hp-guar"), xanthan gum, alginate, chitosan, Gelrite®, hyauluronic acid, dextran, Carbopol® (polyacrylic acid or carbomer) including Carbopol® 900 series including Carbopol® 940 (carbomer 940), Carbopol® 910 (carbomer 910) and Carbopol® 934 (carbomer 934), carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof. In a preferred embodiment the viscosity enhancer will have an equilibration viscosity less than 100 cps, preferably from about 15 to about 35 cps, and most preferably at about 30 cps. In a preferred embodiment the viscosity enhancer is Carbopol® 940 (carbomer 940) at a concentration from about 0.5% to about 6.0% w/v, preferably from about 0.09% to about 1.0% w/v, more preferably at 0.09%, 0.25%, 0.5%, 0.75%, 0.9% or 1.0% w/v. In certain combinations it has been surprisingly discovered nonionic surfactant/viscosity combinations may result in phase separation over time with precipitate formation. In such situations, particularly for polyoxyls, in a preferred embodiment polyoxyl 40 stearate, and cellulose derivatives, particularly hydroxypropyl methyl cellulose, use of a nonpolysaccharide derivative for viscosity enhancement, such as polyacrylic acid derivatives (carbomers, carbomer 934 or 940 in preferred embodiments) may prevent such separation.

It is a discovery of the present invention that several modifications may singly or in combination be used to enhance cold chain stability storage, including in addition to in a preferred embodiment aceclidine 1.40%-1.75%, tropicamide 0.025%-0.10% and optionally a nonioinic surfactant such as polyoxyl 40 stearate 0.5%-10%, preferably 5.5% one or more of (See Table 1):

Acidic pH, preferably less than 5.5, preferably less than 5.0 and most preferably at a pH of about 4.75;

Viscosity enhancer, preferably at 25 C viscosity of about 15-50 cps, and more preferably 20-35 cps, where a preferred embodiment is carbomer 940 0.09%-1.0%;

Addition of a polyol, in a preferred embodiment Mannitol 2.5%-4.0%;

Addition of a buffer, where acetate or phosphate buffers are preferred, 2-100 mmole range with 3-5 mmole is preferred;

Addition of a preservative, where BAK 0.02% is preferred or a combination of BAK, sorbate and borate.

The selective α-2 agonist may be included within the composition of the present invention or applied topically preferably just minutes before or less preferably just minutes afterward if additional means to reduce nasal congestion or redness is desired for sensitive subjects. Selective α-2 agonists suitable for the present invention have minimal α-1 agonist activity at low concentrations. For example, for brimonidine or fadolmidine, 1% to 2% w/v is considered extremely high, 0.5% to 1.0% w/v still highly inductive of α-1 receptors and toxic for purposes of the present invention. Further, 0.10% to 0.5% w/v is still too high and even 0.070% to 0.10% w/v is associated with a higher than preferred incidence of rebound hyperemia (however, for dexmedetomidine, its greater lipophilicity and intraocular penetration reduces rebound risk in this range). Only 0.065% w/v or below is potentially acceptable, where for most α-2 agonists, depending on degree of selectivity 0.050% w/v or even more preferably 0.035% w/v or less is desired. On the other hand some degree of useful activity may occur at one or more orders of magnitude further reduction of concentration. The preferred embodiments, brimonidine, fadolmidine and guanfacine, of the present invention preferentially stimulate α-2 adrenergic receptors, and even more preferably α-2b adrenergic receptors so that α-1 adrenergic receptors are not stimulated sufficiently enough to cause excessive large vessel arteriolar constriction and vasoconstrictive ischemia. In addition, it has been discovered that preventing or reducing redness for drugs that otherwise directly induce redness, such as the acetylcholine agonist, aceclidine, enhances compliance for sensitive subjects that may have induced redness or nasal congestion even with formulations of the present invention that do not include an α-2 agonist. However, because α-2 agonists are shifted to their ionized equilibrium an acidic pH is somewhat offset by the fact such agonists exert greater affect at neutral or alkaline pH. Therefore each α-2 agonist has a preferred pH range depending on its lipophilicity and pKa value when added to the inventive compositions with aceclidine. For the present invention while pH range of 5.0 to 8.0 is tolerated, preferred embodiments are at pH 5.5 to 7.5 and more preferably 6.5 to 7.0. Further, it has been discovered that cyclodextrins and/or polyoxyl 40 stearate as a nonionic surfactant component or as the sole nonionic surfactant, result in a greater whitening effect when the α-2 agonist is included in the composition rather than poloxamer 407. The α-2 agonist may optionally be applied separately or in certain preferred embodiments with formulations of the present invention that do not include an α-2 agonist, such as those formulas with polyoxyl 40 stearate 5.5% w/v as the non-ionic surfactant, although the α-2 agonist is not required except for occasional sensitive subjects. Fadolmidine represents the α-2 agonist with highest hydrophilicity and therefore high surface retention for the present invention. Guanfacine is also highly selective and hydrophilic. Brimonidine is highly selective with moderate lipophilicity. Finally, dexmedetomidine has high selectivity with high lipophilicity that may be used with less efficacy for reducing redness for the purposes of the present invention (although possibly inducing fatigue as a side effect in some patients).

In a preferred embodiment using polyoxyl 40 stearate 5.5% w/v; CMC 0.80% w/v; NaCl 0.037% w/v; EDTA 0.015% w/v, borate buffer 5 mM and BAK 0.007% w/v results in redness of about 1.0 to 1.5 out of 4 which is transient lasting about ten minutes, and by 30 minutes returns to about baseline.

In one embodiment, the selective α-2 adrenergic receptor agonist is a compound which has binding affinity of about 900 fold or greater, even more preferably about 1000 fold or greater, and most preferably, about 1500 fold or greater.

The selective α-2 adrenergic receptor agonist may be present at a concentration from between about 0.0001% to about 0.065% w/v; more preferably, from about 0.001% to about 0.035% w/v; even more preferably, from about 0.01% to about 0.035% w/v; and even more preferably, from about 0.020% to about 0.035% w/v.

In one embodiment, the selective α-2 adrenergic receptor is selected from the group consisting of brimonidine, guanfacine, fadolmidine, dexmedetomidine, (+)-(S)-4-[1-(2,3-dimethyl-phenyl)-ethyl]-1,3-dihydro-imidazole-2-thione, 1-[(imidazolidin-2-yl)imino]indazole, and mixtures of these compounds. Analogues of these compounds that function as highly selective α-2 agonists may also be used in compositions and methods of the present invention.

In a more preferred embodiment, the selective α-2 agonist is selected from the group consisting of fadolmidine, guanfacine and brimonidine. In a yet more preferred embodiment the selective α-2 agonist is brimonidine in the form of a salt at a concentration of 0.025% to 0.065% w/v, more preferably from 0.03% to 0.035% w/v. In a preferred embodiment, the salt is a tartrate salt.

In another yet more preferred embodiment, the selective α-2 agonist is fadolmidine at a concentration from about 0.005% to about 0.05% w/v, more preferably from 0.02% to about 0.035% w/v in the form of a hydrochloride ("HCl") salt.

In another yet more preferred embodiment, the selective α-2 agonist is guanfacine at a concentration from about 0.005% to about 0.05% w/v, more preferably from 0.02% to about 0.035% w/v in the form of an HCl salt.

In another yet more preferred embodiment, the selective α-2 agonist is dexmedetomidine at a concentration from about 0.005% to about 0.05% w/v, more preferably from 0.04% to about 0.05% w/v in the form of an HCl salt.

In another preferred embodiment a pH less than physiologic pH is found to enhance the whitening effect for brimonidine, preferably pH 4.5 to 6.5, and more preferably pH 5.5 to 6.0. However, redness reduction is achieved at all pHs, and enhancement of aceclidine absorption occurs at alkaline pH, such that more effect occurs from a given concentration, and therefore while effective at pH ranges from 4.5 to 8.0, pH range of 6.5 to 7.5 is preferred for the present invention, and 7.0 to 7.5 most preferred.

The present invention is further directed to an opthalmological composition further comprising a cycloplegic agent. It is a surprising and totally unexpected discovery of the present invention that certain cycloplegic agents can be combined with miotic agents, particularly for the present invention, aceclidine, without reducing miotic onset, magnitude, or duration; and further blunt the normally attendant spike in miotic effect coinciding with time of peak absorption in aqueous formulations to provide a constant miosis versus time after onset from 15 to 30 minutes to 6 to 10 hours depending on the desired formulation. The addition of the cycloplegic agent also reduces any residual associated discomfort that may otherwise occur soon after topical instillation, which presumably is a result of ciliary spasms or excessive pupillary miosis.

Cycloplegic agents suitable for the present invention include, but are not limited to, atropine, Cyclogyl® (cyclopentolate hydrochloride), hyoscine, pirenzepine, tropicamide, atropine, 4-diphenylacetoxy-N-methylpiperidine methobromide (4-DAMP), AF-DX 384, methoctramine, tripitramine, darifenacin, solifenacin (Vesicare®; Vesicare is a registered trademark of Astellas Pharma Inc.), tolterodine, oxybutynin, ipratropium, oxitropium, tiotropium (Spriva), and otenzepad (a.k.a. AF-DX 116 or 11-{[2-(diethylamino) methyl]-1-piperidinyl}acetyl]-5,11-dihydro-6H-pyrido[2,3b][1,4]benzodiazepine-6-one). In a preferred embodiment the cycloplegic agent is tropicamide at a concentration from about 0.01% to about 0.10% w/v, more preferably from about 0.025% to about 0.080% w/v and still more preferably from about 0.04% to about 0.06% w/v. In another preferred embodiment the cycloplegic agent is a mixture of tropicamide at a concentration from about 0.04% to about 0.07% w/v or pirenzepine or otenzepad at a concentration from about 0.002% to about 0.05% w/v.

In a preferred embodiment, tropicamide 0.01% w/v was found to slightly reduce brow ache, 0.030% w/v to further reduce brow ache and from 0.04% to about 0.07% w/v to completely eliminate brow ache without reduction of the average pupillary miosis diameter over duration of effect. Tropicamide in preferred embodiments has demonstrated completely unexpected sensitivity of effect, where at about 0.04% w/v unexpectedly and very effectively reduces or eliminates brow ache and ciliary spasm pain, becoming very noticeably further reduced at 0.042% w/v and absent at 0.044% w/v in a preferred embodiment with no cycloplegia (surprising due to its common use as a pupil dilating agent). Yet, tropicamide did not reduce the mean degree of pupil miosis, the time of onset of pupil miosis or the subsequent visual benefits. On the contrary, tropicamide blunted the peak miosis seen in aqueous formulations to create a smooth consistent miotic effect over time. It allowed modulation of peak pupil miosis to achieve a more even effect over time with no dilation as has been found with its prior use. Specifically, tropicamide is useful to prevent transient constriction below 1.50 mm at 30 to 60 minutes following aceclidine in some embodiments and to reduce transient excessive and undesirable dimming of vision that may otherwise occur at peak onset of about 30 minutes. As an example, an opthalmological composition comprising 1.53% w/v aceclidine, 5% w/v HPβCD, 0.75% w/v CMC, 0.25% w/v NaCl, 0.01% w/v BAK and a phosphate buffer at pH 7.0; or 1.45% w/v aceclidine; 5.5% w/v polyoxyl 40 stearate; 0.80% w/v CMC; 0.037% w/v NaCl; 0.015% w/v EDTA; 0.007% w/v BAK and 5 mM phosphate buffer at a pH 7.0; was varied from 0.040% w/v tropicamide, where moderate dimming was noted, to 0.044% w/v tropicamide where dimming became almost undetectable other than in extremely dim light conditions. This additional pupil size modulation with a cycloplegic agent allows aceclidine or pilocarpine concentrations sufficient for prolonged effect while blunting the attendant peak excessive constriction that is undesirable as well as any uncomfortable brow ache. Surprisingly and due to its short-acting nature, tropicamide achieves this blunting effect without causing mydriasis. Further, in a preferred embodiment, tropicamide 0.014% w/v was found to reduce brow ache, 0.021% w/v to further reduce brow ache and from 0.028% to 0.060% w/v and in some embodiments up to 0.09% w/v to completely eliminate brow ache without cycloplegia (i.e. paralysis of ciliary muscle of the eye).

It has been found for a racemic 50:50 mixture of (+) and (−) aceclidine optical isomers (where in some studies (+) is more potent and in others it is felt (−) may be more potent) tropicamide effects may vary depending on the ratio of aceclidine to tropicamide. For example, in an opthalmological composition of the present invention comprising 1.55% w/v aceclidine, 5.5% w/v HPβCD or in a preferred embodiment polyoxyl 40 stearate, 0.75% w/v CMC (1%=2,500 centipoise), 0.25% w/v NaCl, and 0.01% w/v BAK and at pH 7.5, 0.042% w/v tropicamide can be differentiated from even 0.035% w/v, with the former demonstrating normal indoor night vision and the latter slight dimming that becomes more noticeable at still lower concentrations. At higher concentrations, such as from about 0.075% to about 0.090% w/v tropicamide, loss of optimal range pupil constriction 1.50 mm to 1.80 mm range begins, and frank mydriasis at higher concentrations begins to occur. As isomer ratio may alter the effective concentration, this must be factored into the clinical efficacy anticipated using aceclidine; for preferred embodiments of the present invention a polarimeter was used to determine an exact 50:50 isomer ratio was used (personal communication Toronto Research Chemicals).

FIG. 1 shows the effect of a miotic agent with or without a cycloplegic agent and with or without a carrier. Subject is an emmetrope over the age of 45 with a baseline near vision of 20.100 and baseline distance vision of 20.20. Topical administration to the eye of 1% w/v pilocarpine in saline solution results in an improvement of near vision to 20.40 (8a), however this improvement comes at the expense of a reduction in distance vision to 20.100 (8b). The addition of 0.015% w/v tropicamide results in an improvement of near vision to 20.25 (9a) and a lessening of the reduction of distance vision to 20.55 (9b), though in certain instances with some induced irregular astigmatism (mildly blotched areas in reading field of vision). Topical administration of 1.55% w/v aceclidine in saline solution results in an improvement of near vision to 20.40 for an extended time period of 6 hrs (10a) without any effect on the baseline distance vision (10b). 10c and 10d show the effects of administering aceclidine in a carrier composed of 5.5% w/v 2-hydroxypropyl beta cyclodextrin, 0.75% w/v CMC (1%=2,500 centipoise), 0.25% w/v NaCl, and 0.01% w/v BAK. As seen in 10c the carrier increases the beneficial effect of aceclidine resulting in better than 20.20 near vision. As seen in 10d a similar increase in distance vision occurs. 10e and 10f show the effects of adding 0.042% w/v tropicamide to the aceclidine in the carrier. As seen in 10e near vision is improved to 20.15 with a quicker onset of maximum visual acuity. As seen in 10f a similar improvement is seen in distance vision. Taken together, FIG. 1 shows that aceclidine is capable of temporarily correcting near vision in a presbyopic subject without affecting the baseline distance vision. Similar results can be achieved with a different miotic agent, pilocarpine, with the addition of a cycloplegic agent such as tropicamide. A proper drug carrier can also have a beneficial effect.

The present invention is further directed to an opthalmological composition further comprising a tonicity adjustor and a preservative.

A tonicity adjustor can be, without limitation, a salt such as sodium chloride ("NaCl"), potassium chloride, mannitol or glycerin, or another pharmaceutically or opthalmologically acceptable tonicity adjustor. In certain embodiments the tonicity adjustor is 0.037% w/v NaCl, Preservatives that can be used with the present invention include, but are not limited to, benzalkonium chloride ("BAK"), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.007% w/v. In another preferred embodiment the preservative is perborate at a concentration of 0.01% to about 1.0% w/v, more preferably at a concentration of about 0.02% w/v. In another preferred embodiment the preservative is a combination of BAK, sorbate and borate.

Various buffers and means for adjusting pH can be used to prepare opthalmological compositions of the invention. Such buffers include, but are not limited to, acetate buffers, citrate buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 4.0 to about 8.0, more preferably from about 5.0 to about 7.0, even more preferably from about 5.0 to about 6.5 and most preferred from about 5.0 to about 6.0.

The present invention is further directed to an opthalmological composition further comprising an antioxidant. Antioxidants that can be used with the present invention include but are not limited to disodium ethylenediaminetetraacetic acid at a concentration from about 0.005% to about 0.50% w/v, citrate at a concentration from about 0.01% to about 0.3% w/w, dicalcium diethylenetriamine pentaacetic acid ("Ca2DTPA") at a concentration from about 0.001% to about 0.2% w/v, preferably about 0.01% w/v Ca2DTPA which can be formulated by adding 0.0084% w/v Ca(OH)$_2$ and 0.0032% w/v pentetic acid to the formulation and mixing slowly. Further combinations of antioxidants can be used. Other antioxidants that can be used with the present invention include those well known to experts in the art such as ethylenediaminetetraacetic acid at a concentration from about 0.0001% to about 0.015% w/v.

It is a surprising and unexpected discovery that topical formulations of the present invention, particularly one of the preferred embodiments comprising aceclidine 1.35% to 1.55% w/v; 5.5% w/v polyoxyl 40 stearate; 0.80% w/v CMC; 0.037% w/v NaCl; 0.015% w/v EDTA; 0.007% w/v BAK; and 5 mM phosphate buffer at pH 7.0 result in considerably prolonged contact lens wear and comfort after a single topical instillation daily. The single daily use of the preferred embodiments allowed a subject with dry eye to sleep in his lenses for one week periods where previously even after a single night vision would be blurred and contact lenses coated with film requiring removal and cleaning or replacement (see Example 7).

The following representative embodiments are provided solely for illustrative purposes and are not meant to limit the invention in any way.

Representative Embodiments

In another embodiment, the opthalmological composition comprises:
pilocarpine at a concentration of about 1.0% w/v;
tropicamide at a concentration of about 0.012% w/v;
polyoxyl 40 stearate at a concentration of about 5.5% w/v;
carbomer 940 at a concentration of about 0.5% w/v;
citric acid monohydrate at a concentration of about 0.1% w/v; and
acetate buffer at a concentration of about 3 millimolar, wherein said composition has a pH of about 5.

In another embodiment, the opthalmological composition comprises:
pilocarpine at a concentration of about 0.95% w/v;
tropicamide at a concentration of about 0.012% w/v or about 0.015% w/v;
polyoxyl 40 stearate at a concentration of about 3.85% w/v;
carbomer 940 at a concentration of about 0.50% w/v;
citric acid monohydrate at a concentration of about 0.1% w/v; and
acetate buffer at a concentration of about 3.0 millimolar, wherein said composition has a pH of about 5.

In another embodiment, the opthalmological composition comprises:

pilocarpine at a concentration of about 1.50% w/v;
tropicamide at a concentration of about 0.035% w/v;
polyoxyl 40 stearate at a concentration of about 5.5% w/v;
carbomer 940 at a concentration of about 0.385% w/v or about 0.85% w/v;
citric acid monohydrate at a concentration of about 0.1% w/v; and
acetate buffer at a concentration of about 3.0 millimolar,
wherein said composition has a pH of about 5.

In another embodiment, the opthalmological composition comprises:
pilocarpine at a concentration of about 1.50% w/v;
tropicamide at a concentration of about 0.038% w/v;
polyoxyl 40 stearate at a concentration of about 5.5% w/v;
carbomer 940 at a concentration of about 0.385% w/v or about 0.85% w/v;
citric acid monohydrate at a concentration of about 0.1% w/v; and
acetate buffer at a concentration of about 3.0 millimolar,
wherein said composition has a pH of about 5.

In another embodiment, the opthalmological composition comprises:
aceclidine at a concentration of about 1.75% w/v;
tropicamide at a concentration of about 0.042% w/v;
polyoxyl 40 stearate at a concentration of about 4.5% w/v;
mannitol at a concentration of about 2.5% w/v;
acetate buffer at a concentration of about 3.0 mM; and
BAK at a concentration of about 0.02% w/v,
wherein said composition has a pH of about 4.75.

In another embodiment, the opthalmological composition comprises:
aceclidine at a concentration of about 1.55% w/v;
tropicamide at a concentration of about 0.042% w/v;
polyoxyl 40 stearate at a concentration of about 5.5% w/v;
citric acid monohydrate at a concentration of about 0.1% w/v;
mannitol at a concentration of about 4.0% w/v;
Carbopol® (carbomer) 940 at a concentration of 0.09% w/v; and
acetate buffer at a concentration of about 3.0 mM;
wherein said composition has a pH of about 4.75.

In another embodiment, the opthalmological composition comprises:
aceclidine at a concentration of about 1.50% w/v;
tropicamide at a concentration of about 0.042% w/v;
polyoxyl 40 stearate at a concentration of about 5.5% w/v;
mannitol at a concentration of about 2.5% w/v;
phosphate buffer at a concentration of about 3.0 mM;
Carbopol® (carbomer) 940 at a concentration of about 0.25% w/v; and
BAK at a concentration of about 0.02% w/v,
wherein said composition has a pH of about 4.75.

In another embodiment, the opthalmological composition comprises:
aceclidine at a concentration of about 1.45% w/v;
tropicamide at a concentration of about 0.042% w/v;
polyoxyl 40 stearate at a concentration of about 5.5% w/v;
mannitol at a concentration of about 4.0% w/v;
citric acid monohydrate at a concentration of about 0.1% w/v;
acetate buffer at a concentration of about 3.0 mM; and
Carbopol® (carbomer) 940 at a concentration of about 0.75% w/v,
wherein said composition has a pH of about 4.75.

In another embodiment, the opthalmological composition comprises:
aceclidine at a concentration of about 1.45% w/v;
tropicamide at a concentration of about 0.042% w/v;
polyoxyl 40 stearate at a concentration of about 5.5% w/v;
mannitol at a concentration of about 4.0% w/v;
citric acid monohydrate at a concentration of about 0.1% w/v;
phosphate buffer at a concentration of about 3.0 mM; and
Carbopol® (carbomer) 940 at a concentration of about 1.0% w/v,
wherein said composition has a pH of about 4.75.

In another embodiment, the opthalmological composition comprises:
aceclidine at a concentration of 1.5% w/v, mannitol at a concentration of 2.5% w/v.

In another embodiment, the opthalmological composition comprises:
aceclidine at a concentration of 1.55% w/v, mannitol at a concentration of 2.5% w/v.

In another embodiment, the opthalmological composition comprises:
aceclidine at a concentration of 1.6% w/v, mannitol at a concentration of 2.5% w/v.

In another embodiment, the opthalmological composition comprises:
aceclidine at a concentration of 1.65% w/v, mannitol at a concentration of 2.5% w/v.

In another embodiment, the opthalmological composition comprises:
aceclidine at a concentration of 1.7% w/v, mannitol at a concentration of 2.5% w/v.

In another embodiment, the opthalmological composition comprises:
aceclidine at a concentration of 1.75% w/v, mannitol at a concentration of 2.5% w/v.

In another embodiment, the opthalmological composition comprises:
aceclidine at a concentration of 1.48% w/v, mannitol at a concentration of 4.0% w/v and Carbopol® (carbomer) 940 at a concentration of 0.09% w/v.

In another embodiment, the opthalmological composition comprises:
aceclidine at a concentration of 1.48% w/v, mannitol at a concentration of 4.0% w/v and Carbopol® (carbomer) 940 at a concentration of 0.50% w/v.

In another embodiment, the opthalmological composition comprises:
aceclidine at a concentration of 1.48% w/v, mannitol at a concentration of 2.5% w/v and Carbopol® (carbomer) 940 at a concentration of 0.09% w/v.

The following Examples are provided solely for illustrative purposes and are not meant to limit the invention in any way.

EXAMPLES

Example 1—Effect of Aceclidine on Vision of Subjects Aged 47 to 67 Years

Table 1 demonstrates the effect on the near focus ability of presbyopic subjects before and after opthalmological administration of a composition containing aceclidine. Each composition included aceclidine in the concentrations indicated and 5.5% w/v HPβCD, 0.75% w/v CMC, 0.25% w/v NaCl and 0.01% w/v BAK. Additionally compositions administered to subjects 4 and 5 included 0.125% w/v tropicamide. As aceclidine is an enantiomer, the clinical effectiveness may vary with different ratios. For the present studies a nearly exact 50:50 ratio of stereoisomers was measured as best determined by polarimetry.

TABLE 1

Effects of aceclidine on vision of presbyopic patients.

|  |  |  |  | Vision Baseline | | | | Post Gtt 15" | | | | |
| --- | --- | --- | --- | --- | --- | --- | --- | --- | --- | --- | --- | --- |
| Date | # | Age | Aceclidine % | R Pre Dist | L Pre Dist | R Pre Near | L Pre Near | R Post Dist | L Post Dist | R Post Near | L Post Near | Effect (h) |
| Aug. 21, 2013 | 1 | 67 | 1.5 | 20.20 | 20.30 | 20.60 | 20.60 | 20.20 | 20.20 | 20.15 | 20.15 | 9.00 |
| Aug. 22, 2013 | 2 | 52 | 1.5 | 20.30 | 20.30 | 20.50 | 20.50 | 20.25 | 20.25 | 20.25 | 20.20 | 8.00 |
| Aug. 23, 2013 | 3 | 61 | 1.5 | 20.40 | 20.30 | 20.60 | 20.50 | 20.20 | 20.25 | 20.15 | 20.15 | 8.00 |
| Aug. 23, 2013 | 4 | 61 | 1.1 | 20.20 | 20.25 | 20.80 | 20.50 | 20.15 | 20.15 | 20.20 | 20.15 | 12.00 |
| Aug. 23, 2013 | 5 | 53 | 1.1 | 20.20 | 20.20 | 20.60 | 20.60 | 20.20 | 20.20 | 20.25 | 20.25 | 7.00 |
| Aug. 24, 2013 | 6 | 47 | 1.5 | 20.25 | 20.25 | 20.100 | 20.100 | 20.20 | 20.20 | 20.15 | 20.15 | 8.00 |
| Aug. 25, 2013 | 7 | 58 | 1.5 | 20.30 | 20.200 | 20.100 | 20.30 | 20.25 | 20.30 | 20.20 | 20.30 | 8.00 |

As seen in Table 1 all subjects had less than perfect near vision (20.20) in both the left and right eye (object at 15 inches from the eye) and most subjects had less than perfect distance vision before administration of the composition. After administration of the composition all subjects experienced an improvement in their near vision that lasted from 7 to 12 hours. Surprisingly, the majority of subjects also experienced improvement of their distance vision for the same time period. Still more surprisingly the improvement in near point was much closer than 16" typically required for comfortable reading, in some cases to about 8.5" more commonly seen in individuals 30 or less. The addition of tropicamide, a cycloplegic agent, had no additive or deleterious effect on vision correction.

Example 2—Effect of Concentration of Concentration of Aceclidine and Tropicamide

TABLE 2

Effect of concentration of concentration of aceclidine and tropicamide.

|  | #1 | #2 | #3 | #4 | #5 (OD) | #5 (OS) | #6 | #7 |
| --- | --- | --- | --- | --- | --- | --- | --- | --- |
| Brimonidine | 0.03% | 0.03% | 0.03% | 0.03% | 0.03% | 0.03% | 0.03% |  |
| Poloxamer 407 | 5.5% |  |  |  |  |  |  |  |
| HPBCD |  | 5.5% | 5.5% | 5.5% | 5.5% | 5.5% | 5.5% | 5.5% |
| Aceclidine | 1.5% | 1.5% | 0.75% | 1.1% | 1.1% | 1.1% | 1.1% | 1.1% |
| Tropicamide |  |  |  | 0.014% | 0.021% | 0.028% | 0.042% | 0.062% |
| NaCl | 0.25% | 0.25% | 0.25% | 0.25% | 0.25% | 0.25% | 0.25% | 0.25% |
| CMC | 0.75% | 0.75% | 0.75% | 0.75% | 0.75% | 0.75% | 0.75% | 0.75% |
| BAK | 0.1% | 0.1% | 0.1% | 0.1% | 0.1% | 0.1% | 0.1% | 0.1% |
| Redness (15 m) | 3+ | 1 | 0.5 | 0.5 | 0 | 0 | 0 | 0 |
| Redness (30 m) | 1.5 | 0.5 | 0.25 | 0.25 | 0 | 0 | 0 | 0 |
| Brow Ache (60 m) | 2+ | 2+ | 2 | 0.5 | 0.5 | 0.0 | 0.0 | 0.0 |
| Stinging (10 m) | 2 | 2 | 0.5 | 0 | 0 | 0 | 0 | 0 |
| BD-OD | 20.20 | 20.20 | 20.20 | 20.20 | 20.20 | 20.20 | 20.20 | 20.20 |
| BD-OS | 20.25 | 20.25 | 20.25 | 20.25 | 20.25 | 20.25 | 20.25 | 20.25 |
| BN-OD | 8 pt | 8 pt | 8 pt | 8 pt | 8 pt | 8 pt | 8 pt | 8 pt |
| BN-OS | 7 pt | 7 pt | 7 pt | 7 pt | 7 pt | 7 pt | 7 pt | 7 pt |
| BP-photopic | 3 mm | 3 mm | 3 mm | 3 mm | 3 mm | 3 mm | 3 mm | 3 mm |
| BP-mesopic | 5 mm | 5 mm | 5 mm | 5 mm | 5 mm | 5 mm | 5 mm | 5 mm |
| Miosis start (m) | 15 | 15 | 15 | 15 | 15 | 15 | 15 | 15 |
| Miosis (OU) (1 hr) | 1.63 mm | 1.63 mm | 2.0-2.5 mm | 1.63 mm | 1.63 mm | 1.63 mm | 1.63 mm | 1.70 mm |
| Distance (OU) (20 m) | 20.20 | 20.20 | 20.20 | 20.20 | 20.20 | 20.20 | 20.20 | 20.20 |
| Distance (OD) (1 hr) | 20.15 + 2 | 20.15 + 2 | 20.20 | 20.15 + 2 | 20.15 + 2 | 20.15 + 2 | 20.15 + 2 | 20.15 + 2 |
| Distance (OS) (1 hr) | 20.15 + 2 | 20.15 + 2 | 20.20 | 20.15 + 2 | 20.15 + 2 | 20.15 + 2 | 20.15 + 2 | 20.15 + 2 |
| Disance (OU) (1 hr) | 20.10 − 3 | 20.10 − 3 | 20.15 | 20.10 − 3 | 20.10 − 3 | 20.10 − 3 | 20.10 − 3 | 20.10 − 3 |
| Near (OU) (20 m) | 4 pt | 4 pt | 4pt | 4 pt | 4 pt | 4 pt | 4 pt | 4 pt |
| Time (hr) | 12.5 | 12.5 | 6.5 | 11 | 10 | 10 |  |  |

Abbreviations:
(C) indicates corrected vision,
(m) indicates minutes,
(hr) indicates hour,
mm indicates millimeters,
BD indicates baseline distance vision;
BN indicates baseline near vision,
BP indicates baseline pupil size,
OD indicates right eye;
OS indicates left eye and
OU indicates both eyes.

All percentages are w/v. "pt" reflects size of print materials, 4 being equivalent to 20/20 vision and 3 to 20/15 vision.

"Time" refers to duration of the effect.

As seen in Table 2 aceclidine at a concentration of at least 1.1% w/v was able to reduce the size of the pupil to 1.63 mm 1 hour after topical instillation resulting in corrected near and distance vision for at least 10 hours. Lowering of the concentration of aceclidine to 0.75% w/v (formula #3) reduced the miotic effect to 2.0-2.5 mm after 1 hour and vision correction lasted only 6.5 hours. The addition of 0.03% w/v brimonidine reduced redness of the eye (4 out of 4 without brimonidine, not shown) to 1.5 out of 4 within 30 minutes after topical instillation which was maintained for the entire time vision was corrected. Switching the nonionic surfactant to HPβCD (formulas #2-6) further reduced the redness of the eye. Lowering of the concentration of aceclidine to 0.75% w/v (formula #3) further reduced eye redness but as mention above also reduced the vision correction duration of the formula.

A brow ache and stinging in the eye were noticeable in formulas #1-3 with a 2 out of 4 level of pain which was also associated with feelings of slight nausea, upset stomach and fatigue. Surprisingly, the addition of a cycloplegic agent, tropicamide, reduced brow ache and stinging to 0.5 out of 4 and 0 out of 4 respectively with brow ache dissipating after 60 minutes (formula #4). Further, the raising of the concentration of aceclidine to 1.1% w/v restored the longer duration of corrected vision seen in formulas #1-2 without increasing eye redness. However, upon re-topical instillation of formula #4 at the end of the 10 hours noticeable brow ache occurred. Topical instillation of formula #5 (OD) and (OS), with increased tropicamide concentrations, following formula #4 relieved the brow ache experienced with re-instalation of formula #4. Upon a $3^{rd}$ topical instillation, at the end of the effective duration of formula #5, re-topical instillation of formula #5 again led to considerable brow ache. Once again, in formula #6, raising the concentration of tropicamide was able to overcome the brow ache. Additionally and unexpectedly, tropicamide, despite being a cycloplegic agent, had no effect on pupil miosis or vision correction. Surprisingly, the addition of tropicamide resulted in a prolonged duration of optimal pupil size constriction.

To determine the effect of brimonidine on pupil miosis, formula #7, was administered. Administration of formula #7 resulted in only a slight decrease in pupil miosis to 1.70 mm with identical distance and near vision improvement to that of formula #5. A 2-3+ conjunctival injection was noted.

All baseline vision data was based on vision corrected with distance contact lenses. Near vision was noted by subject as outstanding from 8 inches to the horizon at 1.5 hours after installation. A Marco Autorefractor with infrared camera and superimposed pupil calibration scale was used for all pupil size measurements. Once an image was selected it remained on screen allowing accurate calibration.

Example 3—Effect of Concentration of Aceclidine, Brimonidine, Guanfacine, Fadolmidine, Tropicamide and Additives

TABLE 3

Effect of concentration of aceclidine, brimonidine, guanfacine, fadolmidine, tropicamide and additives.

|  | AB2T | AB4T | AB6T | AB11T | AB12T | PROPH13 |
|---|---|---|---|---|---|---|
| Aceclidine | 1.55 | 1.55 | 1.55 | 1.55 | 1.85 | 1.55 |
| Brimonidine | 0.037 | 0.037 | 0.037 | 0.037 |  |  |
| Fadolmidine |  |  |  |  |  | 0.037 |
| Guanfacine |  |  |  |  | 0.037 |  |
| HPBCD | 5.5 | 5.5 | 5.5 | 5.5 | 5.5 | 5 |
| Tropicamide | 0.043 | 0.043 | 0.043 | 0.043 | 0.042 | 0.043 |
| CMC* | 0.075 | 0.075 | 0.075 | 0.075 | 0.075 | 0.075 |
| NaCl | 0.025 | 0.025 | 0.025 | 0.025 | 0.025 | 0.025 |
| BAK | 0.01 | 0.01 | 0.01 | 0.01 | 0.01 | 0.01 |
| Glycerin | 0.1 |  | 0.1 |  |  | 0.1 |
| Poloxamer 188 | 0.1 | 0.05 |  |  |  |  |
| Polyoxyl 40 stearate |  | 0.05 |  |  |  |  |
| pH | 6.5 | 7.5 | 7.5 | 7.5 | 7.0 | 7.5 |
| nasal congestion | 0 | 0 | 0 | 0 | 0 | 0 |
| stinging initial | 0.75 | 0 | 1.5 | 3.5 | 0 | 1.5 |
| stinging, 3 min | 0.5 | 0 | 0 | wash out | 0 | 0 |
| redness initial | 0 | 0 | 1 | D/C | 1 | 1 |
| redness 15 min | 0 | 0 | 0 | D/C | 0 | 0 |
| whitening | 0 | 0 | 0 | D/C | 1.5 | 1.5 |
| pain | 0 | 0 | 0 | D/C | 0 | 0 |
| vision near | 20.30 | 20.15 | 20.15 | D/C | 20.15 | 20.15 |
| vision distance | 20.20 | 20.20 | 20.20 | D/C | 20.20 | 20.20 |
| onset (min) | 20 | 12 | 16 | D/C | 12 | 16 |
| duration (hrs) | 5.5 | 7.5 | 7.5 | D/C | 7.5 | 7.5 |
| color | clear | yellow | yellow | yellow | yellow | yellow |
| OVERALL | 2.5 | 3.9 | 3.8 | 0 | 4 | 3.9 |

*1% = 2,500 cps

All percentages are w/v. Scores for nasal congestion, stinging initial, stinging, 3 min, redness initial, redness 15 min, whitening, pain and overall are out of 4.

"pt" reflects size of print materials, 4 being equivalent to 20/20 vision and 3 to 20/15 vision.

Baseline vision was 20.20 both eyes for distance; 20.70 right eye unaided for near; 20.80 left eye for near (best @ 16").

D/C stands for discontinued after eye washing due to intolerable stinging.

Aceclidine at a concentration of 1.55% w/v was able to reduce the size of the pupil to about 1.63 mm 30 minutes after topical instillation resulting in corrected near and distance vision to 20.20 or better for at least 6 hours, with noticeable affect lasting about 7.5 hours as seen in Table 3. Lowering of the concentration of aceclidine to 1.25% w/v (not shown) resulted in useful near vision improvement to about 20.25-20.30, but not as effective as at the higher dose range alkaline pH resulted in quicker onset, longer duration, and greater effect. The addition of 0.037% w/v brimonidine reduced redness of the eye (4 out of 4 without brimonidine, not shown) to baseline within 15 minutes after topical instillation which was maintained for the about the entire time vision was corrected. Adding glycerin 0.10% w/v noticeably reduced stinging. Adding instead poloxamer 188 0.05% w/v and polyoxyl 40 stearate 0.05% w/v however reduced initial stinging further but was more viscous. The combination of glycerin 0.1% w/v, poloxamer 188 0.1% w/v at a pH of 6.5 was noticeably reduced in onset, duration, comfort and effectiveness. AB11T did not include glycerin, poloxamer 188, or polyoxyl 40 stearate, which resulted in substantial stinging and discontinuation of the experiment with eye flush irrigation immediately after topical instillation. Substitution of guanfacine 0.037% w/v in AB12T for brimonidine resulted in minimal initial redness with prolonged redness reduction and some degree of whitening, and appeared to provide overall the best cosmesis though requiring slightly higher aceclidine concentration for optimal effect.

All baseline vision data was based on vision corrected with distance contact lenses. Near vision was noted by subject as outstanding from 8 to 10 inches to the horizon at 30 minutes after installation for AB4T and AB6T.

AB4T and AB6T were repeated both monocularly and binocularly. Substantial improvement in depth perception, near point acuity to 3 pt (20.15), and near point distance (8", 20.20) was noted when both eyes were treated vs. monocular treatment. Monocular treatment resulted in worsening of vision with both eyes open versus testing only the treated eye.

Example 4—Effect of Concentration of Aceclidine, Brimonidine, Tropicamide, and Additives As seen in Table 4, formulas #8-9, an increase in brimonidine to 0.42% w/v resulted in redness reduction to 0.5, while 0.75% w/v CMC resulted in a watery consistency. Unexpectedly, increasing CMC from 0.75% w/v to a range of 0.80% w/v to 0.87% w/v and increasing NaCl from 0.25% w/v to 0.75% w/v in formulas #10-11 resulted in a thicker consistency and an increased residence time from 7 hours to 10-12 hours and decreased the amount of drug that drained into the nasolacrimal duct. This decreased drug delivery to the nasal passages results in less nasal congestion.

In formulas #13-18 a decrease in the amount of aceclidine from 1.61% to 1.53% w/v resulted in a pupil size range from 1.8-2.0 mm. Dimming as a result of the restriction of the pupil decreased linearly from 1.5 to 0.5 with the decreased amount of aceclidine. Specifically, the 1.8 to 2.0 mm pupil created 41% more light than the 1.5 to 1.7 mm pupil. Surprisingly, the 1.8 to 2.0 mm pupil had a near depth increase of 1.75 D. This is only a 0.25 D loss from the beneficial 2.00 D seen with the 1.5-1.7 mm range. Thus, the 1.80 to 2.0 mm range produces 41% more light while still allowing the full benefit of increased near vision in individuals under 60 years of age; whereas, individuals 60 years of age and over still experience total computer benefit and some increased near benefit.

The increase in tropicamide concentration from 0.042% w/v (formulas #8-#11) to 0.044% w/v (formulas #13-#18) resulted in a decrease in ache to negligible amounts. The

TABLE 4

Effect of concentration of aceclidine, brimonidine, tropicamide, and additives.

|  | #8 | #9 | #10 | #11 | #12 | #13 | #14 |
|---|---|---|---|---|---|---|---|
| Aceclidine | 1.61% | 1.61% | 1.61% | 1.61% | 1.61% | 1.53% | 1.53% |
| Tropicamide | 0.042% | 0.042% | 0.042% | 0.042% | 0.042% | 0.044% | 0.044% |
| Brimonidine | 0.042% | 0.042% | 0.042% | 0.042% |  |  | 0.042% |
| CMC | 0.75% | 0.75% | 0.80% | 0.87% | 0.75% | 0.75% | 0.75% |
| NaCl | 0.25% | 0.25% | 0.50% | 0.50% | 0.25% | 0.50% | 0.50% |
| BAK | 0.01% | 0.01% | 0.01% | 0.01% | 0.01% | 0.01% | 0.01% |
| pH | 7.00 | 7.00 | 7.00 | 7.00 | 8.00 | 7.00 | 7.00 |
| phosphate buffer | 5 mM |  | 5 mM | 5 mM | 6 mM | 5 mM | 5 mM |
| borate buffer |  | 5 mM |  |  |  |  |  |
| Onset (min) | 15 | 15 | 15 | 15 | 15 | 15 | 15 |
| Duration (hrs) | 7 | 7 | 10-12 | 10-12 | 7 | 9 | 7 |
| Pupil range (mm) | 1.5-1.7 | 1.5-1.7 | 1.5-1.7 | 1.5-1.7 | 1.5-1.7 | 1.8-2.0 | 1.8-2.0 |
| Dimming 0-4 | 1.5 | 1.5 | 1.5 | 1.5 | 1.5 | 0.5 | 0.5 |
| Sting 0-4 | 1 | 1 | 1 | 1 | 1 | 1 | 1 |
| Ache 0-4 | 0.25 | 0.25 | 0.25 | 0.25 | 0.25 | 0.00 | 0.00 |
| Redness 0-4 | 0.5 | 0.5 | 0.5 | 0.5 | 1.5 | 1.0 | 0.5 |
| Other | watery | watery | sl thicker | sl residue | watery | watery | watery |
| Overall 0-5 | 3.5 | 3.5 | 4 | 4 | 2.5 | 4.5 | 4.75 |

|  | #15 | #16 | #17 | #18 | #19 | #20 | #21 |
|---|---|---|---|---|---|---|---|
| Aceclidine | 1.53% | 1.53% | 1.53% | 1.53% | 1.45% | 1.65% | 1.75% |
| Tropicamide | 0.044% | 0.044% | 0.044% | 0.044% | 0.042% | 0.044% | 0.035% |
| Brimonidine | 0.042% | 0.042% |  | 0.042% | 0.042% | 0.042% | 0.042% |
| CMC | 0.80% | 0.80% | 0.80% | 0.80% | 0.75% | 0.75% | 0.75% |
| NaCl | 0.50% | 0.75% | 0.75% | 1.00% | 0.25% | 0.25% | 0.25% |
| BAK | 0.01% | 0.01% | 0.01% | 0.01% | 0.01% | 0.01% | 0.01% |
| pH | 7.00 | 7.00 | 8.00 | 7.00 | 7.00 | 7.00 | 8.00 |
| phosphate buffer | 5 mM | 5 mM | 5 mM | 5 mM | 5 mM | 5 mM | 6 mM |
| borate buffer |  |  |  |  |  |  |  |
| Onset (min) | 15 | 15 | 15 | 15 | 15 | 15 | 15 |
| Duration (hrs) | 10-12 | 9 | 9 | 7 | 7 | 7 | 7 |
| Pupil range (mm) | 1.8-2.0 | 1.8-2.0 | 1.8-2.0 | 1.8-2.0 | 1.8-2.1 | 1.8-2.1 | 1.8-2.2 |
| Dimming 0-4 | 0.5 | 0.5 | 0.5 | 0.5 | 0.5 | 0.5 | 0.5 |
| Sting 0-4 | 1 | 1 | 1 | 1 | 1 | 1 | 1 |
| Ache 0-4 | 0.00 | 0.00 | 0.00 | 0.00 | 0.00 | 0.25 | 0.00 |
| Redness 0-4 | 0.5 | 0.5 | 1.0 | 0.5 | 0.5 | 0.5 | 0.5 |
| Other | sl thicker | sl thicker | sl thicker | thicker | watery | watery | watery |
| Overall 0-5 | 5 | 5 | 5 | 4 | 4 | 4 | 4 | amount of ache may also be correlated with the age of the individual. For those individuals under the age of 45, an increase of tropicamide concentration to a range from 0.046% to 0.060% w/v may be preferred.

Further, Table 4 shows an unexpected result seen in formulas #13 and #17 where the increase of NaCl from 0.25% w/v to a range of 0.50 to 0.75% w/v resulted in an acceptable redness score of only 1.0 even without the addition of the redness reducing agent brimonidine.

Formulas #15, #16 and #17 each result in an overall maximum rating of 5 by combining the benefits of: (1) reduced aceclidine concentrations to improve the amount of light produced without significantly affecting the near vision benefits seen in formulas #8-#12; (2) increased NaCl concentrations resulting in a further reduction in redness even in the absence of brimonidine; and (3) increased CMC concentrations resulting in longer residency time on the eye.

Formula #19 is an excellent alternative for the minority of individuals that are high responders to formulas #15-#17 and get noticeable dimming with 1.53% w/v aceclidine. Formula #20 is an excellent alternative for the minority of individuals that are low responders to formula #19. Lastly, Formula #21 is an excellent alternative for the minority of individuals that are low responders and get poor pupil response with Formula #20.

Example 5—Comparison of Effects of Polyoxyl 40 Stearate, HPβCD and Poloxamer 407

TABLE 5

Comparison of Effects of Polyoxyl 40 Stearate, HPβCD and Poloxamer 407.

| | #22 | #23 | #24 |
|---|---|---|---|
| Aceclidine | 1.45% | 1.45% | 1.45% |
| Tropic amide | 0.044% | 0.044% | 0.044% |
| Brimonidine | 0.040% | 0.040% | 0.040% |
| Polyoxyl 40 Stearate | 5.5% | | |
| HPβCD | | 5.5% | |
| Poloxamer 407 | | | 5.5% |
| CMC | 0.80% | 0.80% | 0.80% |
| NaCl | 0.037% | 0.037% | 0.037% |
| EDTA | 0.015% | 0.015% | 0.015% |
| BAK | 0.007% | 0.007% | 0.007% |
| pH | 7.00 | 7.00 | 7.00 |
| phosphate buffer | 5 mM | 5 mM | 5 mM |
| Nasal Congestion | 0.00 | 0.50 | 1.50 |
| Stinging | 0.25 | 0.25 | 0.25 |
| Wetting | 4.00 | 4.00 | 4.00 |
| Redness | 0.25 | 0.50 | 0.50 |
| Visual Blur (<15 sec) | 0.50 | 0.50 | 1.50 |
| Duration | 6-8 hrs | 6-8 hrs | 6-8 hrs |
| Overall 0-4 | 4.00 | 4.00 | 4.00 |

Clinical Protocol 20 presbyopic patients with full distance correction were each given one of the above formulas (#22-#23). All patients received pre- and post-drop distance and near acuity measurement, Zeiss Visante® (Visante is a registered trademark of Carl Zeiss Meditec AG) optical adherence tomography, axial length and contrast acuity testing (i.e. Colenbrander-Michelson 10% Lum target) with the following results:

- all patient achieved a miotic pupil of 1.5 to 2.20 mm;
- no patient experienced ciliary ache, ciliary spasm, or induced accommodation;
- all patients achieved 20/30+ visual acuity or better at 14" and were very satisfied with their high contrast near vision results and there was no significant complaint of burning or aching;
- the duration of effect lasted 6-8 hrs in all cases;
- binocular vision afforded all patients 1-1.5 additional lines of near acuity over monocular testing;
- the last 10 patients were tested at 20" (i.e. computer distance, cell phone distance) and all achieved 20/25 or better near visual acuity;
- moderately hyperopic (approx. +2.25 sphere) uncorrected presbyopes were very satisfied with distance visual acuity that improved to a 20/25 or better level at distance and near vision in the 20/30 range; and
- uncorrected distance acuity was often improved for those patients who chose not to routinely correct a small refractive error.

As seen in Table 5, the use of polyoxyl 40 stearate provides the most comfortable aceclidine formulation with the least amount of visual blur and redness. To achieve similar results to that of formula #22, formula #23 requires 10-15% higher concentrations of the non-ionic surfactant and formula #24 requires 15-20% higher concentrations of the non-ionic surfactant. HPBCD induced a color change over time, possibly indicative of oxidation. Captisol® (sulfobutylether β-cyclodextrin) was substituted with similar findings.

Example 6—Modulation of Aceclidine Concentrations in a Preferred Embodiment

Preferred Embodiment

Aceclidine 1.35%-1.55% w/v;
Polyoxyl 40 stearate 5.5% w/v;
NaCl 0.037% w/v;
a viscosity enhancer, preferably CMC 0.80% w/v or an amount of Carbopol® 934 or 940 sufficient to achieve a viscosity of from about 5 to about 35 cps upon topical instillation, such as Carbopol® 940 at a concentration from about 0.09% to about 1.0% w/v;
BAK 0.02% w/v; and
a phosphate, citrate, citrophosphate, or acetate buffer from about 3 to about 10 mM,
wherein the pH is from about 4.75 to about 6.0.

For 1.35% w/v aceclidine—
Stinging on topical instillation 0.25/4.0 (lasting about 2-5 seconds);
Induced redness at 10 minutes: 1.0 to 1.5/4.0;
Induced redness at 30 minutes: 0.0 to 0.25/4.0;
Comfort: very high.
Wetting: very high, the eye maintaining sensation of improved wetting for most of a 24 hour period after a single topical instillation.
Depth of Focus distance: excellent.
Depth of Focus near: excellent.

In testing the above formulations on several subjects it was discovered that there is a slight range in clinical effect depending on the concentration of aceclidine, where 1.35%-1.55% w/v aceclidine is preferred, but for which 1.35% w/v and 1.45% w/v confer the desired benefits on most subjects.

Further, it is discovered that the clinical effect of 1.35% w/v aceclidine can be improved when instilled as follows:
1) baseline effect: 1 drop to each eye.
2) enhanced effect: 2 drops to each eye.
3) greater effect: after 2) above repeat 1) above.
4) maximum effect: after 2) above repeat 2) above.

Example 7—Use of a Preferred Embodiment to Prolong Contact Lens Wear

Preferred Embodiment

Aceclidine 1.45% w/v;
Polyoxyl 40 stearate 5.5% w/v;
NaCl 0.037% w/v;
a viscosity enhancer, preferably CMC 0.80% w/v or an amount of Carbopol® 934 or 940 sufficient to achieve a viscosity of from about 5 to about 35 cps upon topical instillation, such as Carbopol® 940 at a concentration from about 0.09% to about 1.0% w/v; BAK 0.02% w/v; and
a phosphate, citrate, citrophosphate, or acetate buffer from about 3 to about 10 mM,
wherein the pH is from about 4.75 to about 6.0.

As a baseline, the subject, who normally wore extended wear lenses (Air Optix®; Air Optix is a registered trademark of Novartis AG) for daily wear only, slept in these lenses overnight. On arising each morning the subject's vision was blurred and the contact lenses required removal and cleaning of film and deposits that had formed overnight. Average vision on arising at distance: 20.60; average vision at near on a Michelson contrast acuity chart: 20.80.

Then, for seven consecutive days the above formulation was instilled between 7 am and 10 am each day as a single dose. Subject wore the Air Optix® lenses throughout each day and slept in the lenses overnight. Upon arising each morning the subject's vision at distance: 20.20+; vision at near 20.40 unaided (consistent with subject's baseline presbyopia when the subject did not wear the lenses overnight and instead inserted the lenses upon arising).

Example 8—Comparison of Effects of Polyoxyl 40 Stearate and Captisol® (Sulfobutylether β-Cyclodextrin polyoxyl 40 stearate with Captisol® (sulfobutylether β-cyclodextrin) and adding mannitol achieves similar results in redness reduction as the addition of CAPB to polyoxyl 40 stearate but without the attendant ache resulting in the highest overall rating among aceclidine compositions (Formula #32). After several weeks formulations with Captisol® (sulfobutylether β-cyclodextrin) had an orange hue, possibly indicative of oxidation.

Example 9—Preferred Cold Chain Composition

Composition
aceclidine at a concentration of about 1.40%-1.80% w/v; and
tropicamide at about 0.42% w/v;
polyoxyl 40 stearate at about 5.5% w/v;
mannitol at a concentration of about 2.5% to 4.5% w/v;
carbomer 940 at a concentration of about 0.09% to about 2.0% w/v;
optionally, a preservative such as BAK at a concentration of about 0.2% w/v;
optionally citrate at a concentration of about 0.1%;
optionally with acetate or phosphate buffer at 2-100 mM, more preferably 3-5 mM
wherein said composition has a pH of about 4.50 to about 5.0; and preferably, about 4.75 to about 5.0; and
wherein w/v denotes weight by volume A composition as described above was administered to a 62 year old subject. It resulted in pupils of 1.8-1.9 mm ou, 20.20+ reading vision, and 20.20+ distance vision; whereas without carbomer 940 reduced effectiveness resulted at 2.5% mannitol and no near vision effect resulted at 4.0% mannitol. No ciliary spasm or loss of distance vision resulted. Onset was within about 15 minutes. Transient redness of about 1+/out of 4 was noted for about 20 minutes without alpha agonist vasoconstrictor. The presence or absence of BAK had no clinical effect, and was used to provide an optional preservative.

TABLE 6

Comparison of Effects of Polyoxyl 40 Stearate and Captisol ® (sulfobutylether β-cyclodextrin).

|  | #25 | #26 | #27 | #28 | #29 | #30 | #31 | #32 | #33 |
|---|---|---|---|---|---|---|---|---|---|
| Aceclidine | 1.35% | 1.35% | 1.35% | 1.35% | 1.35% | 1.35% | 1.35% | 1.35% | 1.35% |
| Tropicamide | 0.044% | 0.044% | 0.044% | 0.044% | 0.044% | 0.044% | 0.044% | 0.044% | 0.044% |
| Polyoxyl 40 stearate | 5.5% | 5.5% | 5.5% | 5.5% | 5.5% | 5.5% | 5.5% |  |  |
| Captisol ® |  |  |  |  |  |  |  | 5.5% | 5.5% |
| Cocamidopropyl betaine |  |  |  |  |  |  | 0.10% |  |  |
| EDTA |  |  | 0.015% | 0.015% | 0.005% | 0.005% | 0.005% | 0.005% | 0.015% |
| CMC 1% = 2,500 cps | 0.80% | 0.80% | 0.80% | 0.80% | 0.80% | 0.80% | 0.80% | 0.80% | 0.80% |
| NaCl | 0.037% | 0.037% | 0.037% | 0.037% | 0.037% | 0.037% | 0.037% | 0.037% | 0.037% |
| Mannitol |  |  |  |  |  |  |  | 4% | 4% |
| BAK | 0.007% | 0.007% | 0.007% | 0.007% | 0.007% | 0.007% | 0.007% | 0.007% | 0.007% |
| Borate buffer (mM) | 4 |  | 4 |  | 4 | 4 | 4 | 4 | 4 |
| Phosphate buffer (mM) |  | 4 |  | 4 |  |  |  |  |  |
| pH | 7 | 7 | 7 | 7 | 7 | 7 | 7 | 7 | 7 |
| Redness, 10 min | 1.25 | 1.25 | 2 | 2 | 1.75 | 1.75 | 0 | 0 | 0 |
| Redness, 30 min | 0 | 0 | 1.5 | 1.5 | 1.25 | 1.25 | 0 | 0 | 0 |
| Pupil, 30 min (mm) | <2 | <2 | <2 | <2 | <2 | <2 | <2 | <2 | <3 |
| Blur on instill (sec) | 10 | 10 | 10 | 10 | 10 | 10 | 10 | 10 | 10 |
| Ache | 0 | 0 | 0 | 0 | 0 | 0 | 1 | 0 | 0 |
| Rating | 4.00 | 4.00 | 2.00 | 2.00 | 2.50 | 2.50 | 1.00 | 5.00 | TBD |

As seen in Table 6, when using polyoxyl 40 stearate as the surfactant the exclusion of EDTA results in reduced redness and best overall rating among polyoxyl 40 stearate compositions (Formulas #25 and #26). The addition of cocamidopropyl betaine ("CAPB") further reduces redness however results in significant ache (Formula #31). Replacing

Example 10—Stabile Aceclidine Formulations

Composition Tested:
aceclidine at a concentration of about 1.50% w/v;
tropicamide at a concentration of about 0.042% w/v;
polyoxyl 40 stearate at a concentration of about 5.5% w/v;

mannitol at a concentration of about 2.5% w/v;
citrate at a concentration of about 3 mM;
wherein said composition has a pH of about 4.75.

20 samples of the above composition were divided evenly and stored at 25° C. and 4° C. Prior to storage, initial concentrations of aceclidine were measured using high-pass liquid chromatography ("HPLC"). The amount of aceclidine in each solution was calculated by the area under the principal peak compared to a reference solution of aceclidine. Samples were then subject to storage for 3 months. Aceclidine measurements were taken at 1, 2 and 3 months. Results of the stability test are shown in Table 7.

TABLE 7

Stability of Aceclidine in Cold Chain Storage

|  | 25° C. | 4° C. |
| --- | --- | --- |
| Initial | 100% | 100% |
| 1 month | 92% | 93% |
| 2 months | 75% | 92% |
| 3 months | 50% | 88% |

As seen in Table 7 "cold chain storage" or storage of the aceclidine composition at from 2° C. to 8° C. resulted in a significant increase in stability of aceclidine at all 3 time points.

Example 11—Improved Distance Vision Using Separate Aceclidine and Diluent Formulations First Container or Chamber:
aceclidine at a concentration of about 1.50% w/v lyophilized with
mannitol as a cryoprecipitate at a concentration of about 2.5% w/v;
Second Container or Chamber:
tropicamide at a concentration of about 0.042% w/v;
polyoxyl 40 stearate at a concentration of about 5.5% w/v;
optionally citrate at a concentration of about 0.1% w/v;
optionally BAK as a preservative at a concentration of about 0.02% w/v.

6 subjects were given a Snellen Chart vision exam and their results were recorded and reproduced in Table 8 below. These 6 subjects were then administered a dose of a composition immediately above. The 6 subject were then retested 10 minutes, 1 hour, 2 hours and 4 hours and 8 hours after administration.

TABLE 8

Distance Vision Improvement

| Eye | Before | | After (10 min) | | After (1 hr) | | After (2 hrs) | | After (4 hrs) | | After (8 hrs) | |
| --- | --- | --- | --- | --- | --- | --- | --- | --- | --- | --- | --- | --- |
| | Left | Right | Left | Right | Left | Right | Left | Right | Left | Right | Left | Right |
| #1 | 20.20 | 20.20 | 20.15 | 20.15 | 20.15 | 20.15 | 20.15 | 20.15 | 20.15 | 20.15 | 20.15 | 20.15 |
| #2 | 20.800 | 20.400 | 20.50 | 20.50 | 20.50 | 20.50 | 20.50 | 20.50 | 20.50 | 20.50 | 20.50 | 20.50 |
| #3 | 20.100 | 20.200 | 20.15 | 20.20 | 20.15 | 20.20 | 20.15 | 20.20 | 20.20 | 20.20 | 20.20 | 20.20 |
| #4 | 20.50 | 20.40 | 20.15 | 20.15 | 20.15 | 20.15 | 20.15 | 20.15 | 20.15 | 20.15 | 20.15 | 20.15 |

As seen in Table 8 the administration of a composition comprising aceclidine and tropicamide to the eye of subjects with either perfect (20.20) or less than perfect distance vision (20.>20) resulted in improvement of distance vision. Among those with perfect distance vision the improvement was as great as 30% (subject #1). Among those with less than perfect distance vision the improvement was as great as 1500% (subject #2).

Example 12—Effects of Mannitol and Carbopol® 940 on Pupil Size, Distance Vision and Near Vision

TABLE 9

Effects of Mannitol and Carbopol® 940

| | A | B | C | D | E | F |
| --- | --- | --- | --- | --- | --- | --- |
| Aceclidine | 1.42% | 1.50% | 1.50% | 1.48% | 1.65% | 1.75% |
| Tropicamide | 0.042% | 0.042% | 0.042% | 0.042% | 0.042% | 0.042% |
| Polyoxyl 40 stearate | 5.50% | 5.50% | 5.50% | 5.50% | 5.50% | 5.50% |
| Mannitol | | 2.50% | 4.00% | 4.00% | 2.50% | 2.50% |
| Citrate Buffer | | pH 5.0 | | | | |
| Citrate only | 0.10% | | 0.10% | 0.10% | 0.10% | 0.10% |
| Acetate buffer pH 4.75 | 3 mM | | 3 mM | 3 mM | 3 mM | 3 mM |
| BAK* | 0.01% | 0.01% | 0.01% | 0.01% | 0.01% | 0.01% |
| Carbopol® 940 | | | | 0.09% | | |
| HPMC | 0.30% | | | | | |
| Pupil (mm) 1 hr | 1.8 | 2.1 | 2.4 | 1.9 | 2 | 1.9 |
| VA cc D | | | | | | |
| Pre | 20.20 | 20.20 | 20.20 | 20.20 | 20.20 | 20.20 |
| Post | 20.15+ | 20.20+ | 20.20 | 20.15+ | 20.15+ | 20.15+ |
| VA sc N | | | | | | |
| Pre | 8 pt | 8 pt | 8 pt | 8 pt | 8 pt | 8 pt |
| Post | 5 pt | 6 pt | 8 pt | 5 pt | 6 pt | 5 pt |
| Duration (hrs) | 6.5 | 5.5 | 5.5 | 6.5 | 6 | 6 |

VA = visual acuity
cc = with correction
sc = without correction
D = distance vision
N = near vision
*BAK may also be at 0.02%

Pupil size based on direct Orbscan® and Marco pupillometry video screen calibration (Orbscan is a registered trademark of Technolas Perfect Vision GMBH).

As shown when comparing formulas A, B and C the addition of mannitol resulted in reduced pupil miosis and less distance and near unaided vision improvement; but this suppression was largely neutralized by addition of Carbopol® 940 (formula D; 0.18% and 0.50% Carbopol® 940 resulted in similar effects as 0.09%, data not shown) or increasing the aceclidine concentration from about 1.40% to about 1.60%-1.75%.

Example 13—Predicted 25° C. Stable Aceclidine Formulations

Composition:
aceclidine at a concentration of about 1.48% w/v;
tropicamide at a concentration of about 0.042% w/v;
polyoxyl 40 stearate at a concentration of about 5.5% w/v;
mannitol at a concentration of about 2.5% w/v;
Carbopol® 940 (carbomer 940) at a concentration of about 0.09% w/v;
optionally citrate at a concentration of about 0.2% w/v;
optionally acetate or phosphate buffer at a concentration of about 3.0 mM;
optionally a preservative such as BAK at a concentration of about 0.02% w/v;
wherein said composition has a pH of about 4.75.

Composition:
aceclidine at a concentration of about 1.48% w/v;
tropicamide at a concentration of about 0.042% w/v;
polyoxyl stearate at a concentration of about 4.0% w/v;
mannitol at a concentration of about 4.0% w/v;
Carbopol® 940 (carbomer 940) at a concentration of about 0.09% w/v;
optionally citrate at a concentration of about 0.2% w/v;
optionally acetate buffer at a concentration of about 3.0 mM;
optionally a preservative such as BAK at a concentration of about 0.02% w/v;
wherein said composition has a pH of about 4.75.

Example 14—Dual-Chamber Delivery

General Formula:
Lyophilized Composition:
Aceclidine 1.55%-1.75% w/v
Mannitol 2.5% w/v
Diluent Composition:
Tropicamide 0.042% w/v
Polyoxyl 40 stearate 5.5% w/v
Carbopol® 940 0.09% to 1.0% w/v, preferably 0.5% to 0.9% w/v
BAK 0.02% w/v
Citrate, phosphate or acetate buffer at pH 4.75-5.0 3 mM-100 mM.

Formula II:
Lyophilized Composition:
Aceclidine 1.65% w/v
Mannitol 2.5% w/v
Diluent Composition:
Tropicamide 0.042% w/v
Polyoxyl 40 stearate 5.5% w/v
Optionally BAK 0.02% w/v or a combination of BAK, sorbate and borate
Citrate buffer at 3 mM
pH of 5.0

Formula III:
Lyophilized Composition:
Aceclidine 1.75% w/v
Mannitol 2.5% w/v
Diluent Composition:
Tropicamide 0.042% w/v
Polyoxyl 40 stearate 5.5% w/v
Optionally citrate 0.1% w/v
Optionally BAK 0.02% w/v
Optionally acetate, citrate, citrophosphate or phosphate buffer at 3 to 10 mM
pH of 4.75 to 5.5.

Method

Aceclidine can be packaged in a convenient dual chamber unit dose pack allowing complete mixing prior to installation. An assembly comprising two chambers of a unit-dose container are separated by an impermeable thin membrane, or thick membrane with thin central region. Aceclidine is lyophilized with mannitol as a cryoprecipitate and placed within the base of the unit dose container and sealed at its end creating a lyophilized chamber (first chamber). Preferably the lyophilized chamber is vacuum sealed and/or purged of air with nitrogen gas both before and while being sealed. An opthalmologically effective diluent formulation as listed above is placed at the apex of the unit dose and sealed at its end creating a diluent chamber (second chamber). The user may then simply pinch the diluent chamber firmly, creating a break in the impermeable membrane between the lyophilized chamber and diluent chamber and releasing the lyophilized aceclidine into the diluent chamber with premixing resulting in a suspension or a solubilized solution prior to subject topical instillation.

The assembly may be optionally designed to effect an automatic compression of the diluent chamber causing the impermeable membrane to rupture and deliver the drug into the diluent chamber. An example of such an automatic compression may occur by placing the unit dose packs in a rack assembly where an upper plastic planar assembly is designed with a smaller opening than the diameter of the unit dose pack at its apex (i.e. the diluent chamber), wherein pulling a tab of the unit dose may then squeeze the upper chamber and effect its internal rupture and mixing of the lyophilized tyrosine kinase inhibitor and opthalmologically effective diluent. Alternatively, the puncturing of the impermeable membrane is effected by the turning of a screw cap thus mixing the lyophilized aceclidine with the preferred diluent.

Example 15—Use of Preferred Embodiment for Dual-Chamber Delivery

Formula
Vial A: Lyophylized Powder
1.65% w/v aceclidine
2.5% w/v mannitol
Vial B: Diluent
0.042% w/v tropicamide
5.5% w/v polyoxyl 40 stearate
0.01% w/v BAK or a combination of BAK, sorbate and borate
3 mM citrate buffer
pH 5.0

Method

One cubic centimeter ("cc") of diluent from Vial B was injected into Vial A and the lyophilized powder was allowed to completely solubilize over several minutes. Two drops were then administered to each eye via a 3 cc syringe with the needle removed. Acuity measurements were then taken in a room whose sole illumination was produced by the backlit visual acuity charting, where pupil measurement was taken 3 meters back with fellow eye viewing the illuminated chart. A Neuroptix pupillometer was used for all pupil readings. A neutral density filter of 3 cd/m was placed over the illumination chart for dim illumination low contrast acuity testing. Distance vision was tested at 3 meters (m) using a chart designed for that distance. Near vision was tested at 40 cm, 66 cm, and 100 cm binocularly.

TABLE 10

Visual Acuity after Topical Instillation of Dual-Chamber Aceclidine Composition

| Test | LogMAR | | |
|---|---|---|---|
| | OD | OS | OU |
| Baseline Pupil Size (mm) | 4.20 | 4.3 | — |
| 15 min after instillation | 1.90 | 1.9 | — |
| 30 min after instillation | 2.10 | —* | — |
| Baseline Distance (3 m) | 0.14 | 0 | — |
| 0.25 h Distance (3 m) | −0.08 | −0.1 | — |
| 0.5 h Distance (3 m) | −0.1 | 0 | — |
| 1 h Distance (3 m) | −0.18 | −0.1 | — |
| Baseline Low-luminance | 0.3 | 0.14 | — |
| 0.25 h Low-luminance | 0.08 | 0.08 | — |
| 0.5 h Low-luminance | 0.12 | 0.08 | — |
| 1 h Low-luminance | 0.02 | 0.08 | — |
| Baseline 40 cm | 0.46 | 0.18 | 0.2 |
| 0.25 h 40 cm | — | — | 0.12 |
| 0.5 h 40 cm | — | — | 0.02 |
| 1 h 40 cm | — | — | 0 |
| Baseline 66 cm | 0.08 | 0.04 | −0.02 |
| 0.25 h 66 cm | — | — | −0.12 |
| 0.5 h 66 cm | — | — | −0.14 |
| 1 h 66 cm | — | — | −0.12 |
| Baseline 100 cm | 0.06 | 0.02 | −0.08 |
| 0.25 h 100 cm | — | — | −0.14 |
| 0.5 h 100 cm | — | — | −0.18 |
| 1 h 100 cm | — | — | −0.2 |

Abbreviations:
m indicates meters,
mm indicates millimeters,
cm indicates centimeters,
h indicates hour,
OD indicates right eye;
OS indicates left eye and
OU indicates both eyes.
LogMAR is a visual acuity chart specialized for research settings. LogMAR values approximate to Snellen Chart values as follows: 1.00 (20/200), 0.90 (20.160), 0.80 (20.125), 0.70 (20.100), 0.60 (20.80), 0.50, (20.63), 0.40 (20.50), 0.30 (20.40), 0.20 (20.32), 0.10 (20.25), 0.00 (20.20), −0.10 (20.16), −0.20 (20.13), −0.30 (20.10).
*indicates failure of the Neuroptix pupillometer.

As indicated in Table 10 instillation of the dual-chamber aceclidine composition resulted in improved distance vision, near vision and low-light vision. Specifically, distance vision gradually improved from 0.14 (about 20.28) in the left eye to −0.18 (about 20.13) and from 0.00 (20.20) in the right eye to −0.1 (20.16). Distance vision in low light improved from 0.3 (20.40) in the left eye to 0.02 (about 20.21) and from 0.14 (about 20.28) in the right eye to 0.08 (about 20.24). Near vision at 40 cm (16 inches) improved from about 0.2 (20.32) to 0 (20.20). Near vision at 66 cm (26 inches) improved from about −0.02 (about 20.19) to −0.12 (about 20.15). Near vision at 100 cm (39 inches) improved from about −0.08 (about 20/17) to −0.2 (20.13).

Example 16—Correction of Presbyopia with No Reduction of Distance Vision

Formulation:
pilocarpine at a concentration of about 1.25% w/v
tropicamide at a concentration of about 0.035% w/v
polyoxyl 40 stearate at a concentration of about 5.5% w/v
carbomer 940 at a concentration of about 0.50% w/v
citric acid monohydrate at a concentration of about 0.10% w/v
acetate buffer at a concentration of about 3.0 millimolar
pH of about 5.

1 drop of the above formulation was instilled into the right eye of the patient. Prior to instillation, the patient had a near vision acuity of 20.60 and a distance vision acuity of 20.20 with distance vision corrective lenses. After instillation of the above formulation, the patient had a near vision acuity of 20.30 and a distance vision acuity of 20.20. The corrected near vision was not accompanied by any ciliary spasm and had a redness of about 0.5. Post-instillation pupil size was estimated to be about 2.0 to 2.2 millimeters. Compared to prior art pilocarpine use, the above formulation surprisingly and unexpectedly resulted in no reduction in distance vision and was not accompanied by side effects such as ciliary spasm.

Example 17—The Effect of Myopic Spherical Equivalent Fraction on Distance Vision Acuity at Various Pupil Sizes Method A subject with a best corrected 20.15 acuity eye was subject to refractive correction from 0.0 diopters ("D") to the myopic targets indicated (−0.5 D to −6 D). At all diopters tested the subject was topically administered a combination of aceclidine and tropicamide to adjust pupil size.

Results

Figure 2:
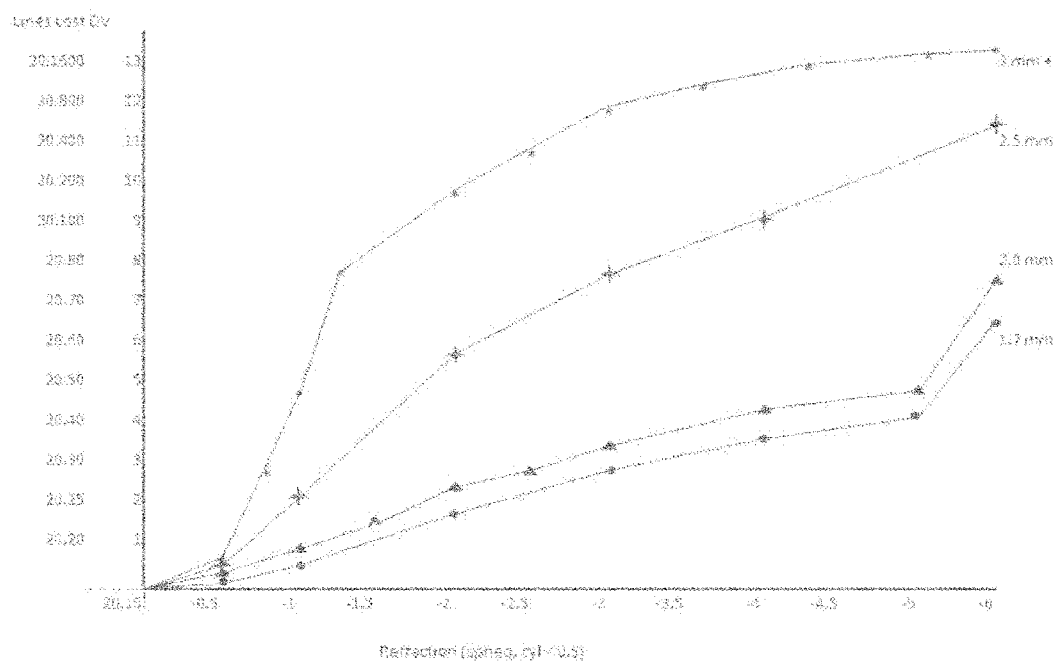
FIG. 2 is a graphical representation of the effects of myopic spherical equivalent fraction on distance vision acuity at various pupil sizes.

At a pupil size above 2.5 mm only modest pinhole optical correction of distance vision was seen, and at 3.0 mm or above essentially no correction was seen. See FIG. 2. At a pupil size below 2.0 mm there is modest continued improvement in distance vision, but below 1.60 mm dimming becomes considerable and distance acuity was not measured. Importantly, at or above −1 D, 1 line of vision is lost, whereas at 0.50 D vision loss is barely detectable. The implications of this are, though not wishing to be held to particular theory, important considerations of the present invention:

a. as a general observation, pinhole optics substantially correct refractive error at or about 2.0 mm or less;
  b. the improvement is degraded by about 1 line of vision or more once additional or induced miosis of 1.0 D or more occurs;
  c. 0.50 D of induced myopia has little effect on distance vision for a 1.7-2.0 mm pupil;
  d. the present invention demonstrates that pupil sizes ranging from about 1.7-2.1 mm result in substantial near vision improvement with no demonstrable accommodation;
  e. the ability to dissociate ciliary contraction from pupillary miosis sufficient to create a 1.7-2.1 mm pupil range, with induction of about, but no greater than, 0.50 D of accommodation results in excellent distance vision, pinhole optic enhanced near vision, and additive accommodative near vision improvement; and
  f. because the presbyopic range for ages 45 to 55 for example is +1.00 to +1.50 for emmetropes, the additive benefit of 0.50 D of accommodative tone might further enhance near vision improvement without deleterious effect on distance.

Example 18—Effect of Pilocarpine and Tropicamide Formulas on Near and Distance Vision and Pupil Size Formulas
Formula #34:
Pilocarpine 1.00% w/v
Tropicamyl 0.042% w/v
Polyoxyl 40 stearate 5.5% w/v
Citric Acid 0.10% w/v
Carbopol 0.85% w/v
Acetate buffer 3 mM pH 5.0
Formula #35:
Pilocarpine 1.50% w/v
Tropicamide 0.035% w/v
Polyoxyl 40 stearate 5.5% w/v
Citric Acid 0.10% w/v
Carbopol 0.85% w/v
Acetate buffer 3 mM
pH 5.0

Method

Formula #34 and Formula #35 were each instilled at separate times in the eye of a subject, which had 20.20 distance vision acuity and 20.40 near vision acuity and a pupil size of 5 millimeters. Distance and near vision were checked using Jaeger near charts and Snellen distance acuity charts at the times indicated in Table 11. Pupil size was measured using an Orbscan® Hz with no room illumination or adjustment for measured pupil size and compared with a Marco video caliper adjusted scale.

Results

Formula #34 constricted the pupil to 3.5 mm at 1 hour with a peak of 3 mm at 4 hours post instillation. Installation of Formula #34 had no effect on either near or distance vision. Not wishing to be held to particular theory, this is believed to be due to insufficient pupillary constriction for enhanced depth of focus. Slight pupil miosis occurred 40 minutes after instillation and resulted in only slight ciliary sensation and redness and no discomfort beyond a medium discomfort for 15 seconds following instillation. See Table 11.

Formula #35 constricted the pupil to 1.9 mm after 1 hour and maintained constriction to 2 mm and 2.1 mm at 4 and 6 hours, respectively. Installation of Formula #35 resulted in improvement of distance vision to 20.15 for 5 hours, which returned to 20.20 at 7 hours. Further, instillation of Formula #35 resulted in improvement of near vision to 20.20 at 4 hours, 20.25 at 7 hours and 20.30 at 8 hours post instillation. Pupil miosis occurred 20 minutes after instillation and resulted in only slight ciliary sensation and redness and no discomfort beyond a medium discomfort for 15 seconds following instillation. See Table 11.

TABLE 11

Effect of Pilocarpine and Tropicamide Formula on Vision and Pupil Size

| | Formula | |
|---|---|---|
| | #34 | #35 |
| DBVCA baseline | 20.20 | 20.20 |
| DBVCA 1 hour * | 20.20 | 20.15 |
| DBVCA 2 hours * | 20.20 | 20.15 |
| DBVCA 3 hours * | 20.20 | 20.15 |
| DBVCA 4 hours * | 20.20 | 20.15 |
| DBVCA 5 hours * | 20.20 | 20.15 |
| DBVCA 7 hours * | 20.20 | 20.20 |
| DCNVA baseline | 20.40 (J4) | 20.40 (J4) |
| DCNVA 1 hour * | No Change | 20.20 (J1) |
| DCNVA 2 hours * | No Change | 20.20 (J1) |
| DCNVA 3 hours * | No Change | 20.20 (J1) |
| DCNVA 4 hours * | No Change | 20.20 (J1) |
| DCNVA 5 hours * | No Change | 20.25 (J2) |
| DCNVA 7 hours | No Change | 20.25 (J2) |
| DCNVA 8 hours | No Change | 20.30 (J3) |
| Pupil (mm) baseline | 5 | 5 |
| Pupil 1 hour | 3.5 | 1.9 |
| Pupil 4 hours | 3 | 2 |
| Pupil 6 hours | | 2.1 |
| Onset (min) | 40 | 20 |

TABLE 11-continued

Effect of Pilocarpine and Tropicamide Formula on Vision and Pupil Size

| | Formula | |
|---|---|---|
| | #34 | #35 |
| Duration (decay point, hrs) | 0 | 7, 8 |
| Ciliary Sensation (BA) | 0.5 | 0.5 |
| Redness (R) | 0.5 | 0.5 |
| Comfort (C) | 4 | 4 |
| Other | Sting 2.5 + for 15 sec | Sting 2.5 + for 15 sec |

BA = ciliary sensation: 0.5 slight sharp well tolerated sensation, 1.0 discomfort, 2.0-4.0 definite pain to intolerable
R = redness 0-4 scale, where 1 = trace, 2 = moderate, 3 = severe, 4 = chemosis (swelling and redness)
C = comfort 0-4 scale where 4 = max totally comfortable; where initial drop effect 1$^{st}$ seconds measured as other.

Formula #35 is an improvement over the use of a formula containing 1% pilocarpine and 0.12% oxymetazoline as described in U.S. Patent Application Publication No. 2014/0113946 ("Allergan® Formula"). Specifically, the Allergan® Formula resulted in near vision correction of 3.5 lines up to 4 hours after instillation and 2.1 lines of correction at 6 hours post instillation. Installation of Formula #35 resulted in comparable, yet longer lasting, near vision correction with 3 lines of correction up to 4 hours after instillation and 2 lines of correction at more than 7 hours post instillation.

Further, instillation of Formula #35 resulted in an unexpected and marked improvement in distance vision over the Allergan® Formula. Specifically, instillation of the Allergan® Formula resulted in a deterioration in distance vision of −0.65 lines (26% reduction) for up to 4 hours; whereas instillation of Formula #35 resulted in an improvement of distance vision of 0.7 lines (26% increase) for more than 5 hours.

Example 19—Effect of Another Pilocarpine and Tropicamide Formula on Near and Distance Vision and Pupil Size Formula
Formula #36:
Pilocarpine 1.25% w/v
Tropicamide 0.035% w/v
Polyoxyl 40 stearate 5.5% w/v
Citric Acid 0.10% w/v
Carbopol 0.85% w/v
Acetate buffer 3 mM
pH 5.0

Method

Formula #36 was applied under the same experimental conditions as in Example 18.

Results

Instillation of Formula #36 resulted in improvement of distance vision to 20.15 for 2 hours. Further, instillation of Formula #36 resulted in an onset of about 30 minutes for near vision enhancement with a maximum improvement to about J2 at 1 hour (20.25 near). After about four hours the enhanced distance and near vision effects rapidly diminished.

What is claimed is:

1. An opthalmological composition for the treatment of presbyopia comprising from about 0.5% to about 2.5% w/v of a muscarinic agonist and a cycloplegic agent, wherein w/v denotes weight by volume.

2. The composition of claim 1 wherein the muscarinic agonist is selected from the group consisting of pilocarpine, aceclidine, carbachol, talsaclidine, sabcomeline, cevimeline, WAY-132983, AFB267B (NGX267), AC-42, AC-260584, 77-LH-28-1, and LY593039 or a pharmaceutically acceptable salt, ester, or prodrug thereof.

3. The composition of claim 1 wherein the cycloplegic agent is selected from the group consisting of pirenzepine, tropicamide, cyclopentolate hydrochloride, 4-diphenylacetoxy-N-methylpiperidine methiodide (4-DAMP), AF-DX 384, methoctramine, tripitramine, darifenacin, solifenacin, tolterodine, oxybutynin, ipratropium, oxitropium, tiotropium, otenzepad and a combination thereof.

4. The composition of claim 1 wherein the ratio of muscarinic agonist to cycloplegic agent is greater than about 25:1.

5. The composition of claim 4 wherein the ratio of muscarinic agonist to cycloplegic agent is greater than about 40:1.

6. A method of treating presbyopia comprising administering a therapeutically effective amount of a composition of claim 1 to a patient in need thereof.

7. The method of claim 6 wherein distance vision acuity of the patient is not reduced.

8. An opthalmological composition for the treatment of presbyopia comprising from about 0.5% to about 2.5% w/v pilocarpine or a pharmaceutically acceptable salt, ester, or prodrug thereof and a cycloplegic agent, wherein w/v denotes weight by volume.

9. The composition of claim 8 wherein the cycloplegic agent is selected from the group consisting of pirenzepine, tropicamide, cyclopentolate hydrochloride, 4-diphenylacetoxy-N-methylpiperidine methiodide (4-DAMP), AF-DX 384, methoctramine, tripitramine, darifenacin, solifenacin, tolterodine, oxybutynin, ipratropium, oxitropium, tiotropium, otenzepad and a combination thereof.

10. The composition of claim 8 wherein the cycloplegic agent is at a concentration from about 0.010% to about 0.1% w/v.

11. The composition of claim 10 wherein pilocarpine is at a concentration of about 1.5% w/v.

12. A method of treating presbyopia comprising administering a therapeutically effective amount of a composition of claim 8 to a patient in need thereof.

13. The method of claim 12 wherein distance vision acuity of the patient is not reduced.

14. An opthalmological composition for the treatment of presbyopia comprising from about 0.5% to about 2.5% w/v pilocarpine or a pharmaceutically acceptable salt, ester, or prodrug thereof and tropicamide, wherein w/v denotes weight by volume.

15. The composition of claim 14 wherein tropicamide is at a concentration from about 0.010% to about 0.1% w/v.

16. The composition of claim 15 wherein pilocarpine is at a concentration of about 1.5% w/v and tropicamide is at a concentration of about 0.035% w/v.

17. The composition of claim 15 wherein pilocarpine is at a concentration of about 0.95% w/v and tropicamide is at a concentration of about 0.015% w/v.

18. A method of treating presbyopia comprising administering a therapeutically effective amount of a composition of claim 14 to a patient in need thereof.

19. The method of claim 18 wherein distance vision acuity of the patient is not reduced.

* * * * *